(12) United States Patent
Castro

(10) Patent No.: US 7,640,680 B1
(45) Date of Patent: Jan. 5, 2010

(54) PEDORTHIC SYSTEMS

(76) Inventor: Ernesto G. Castro, 1306 E. Main St., Mesa, AZ (US) 85203

(*) Notice: Subject to any disclaimer, the term of this patent is extended or adjusted under 35 U.S.C. 154(b) by 538 days.

(21) Appl. No.: 11/231,489

(22) Filed: Sep. 20, 2005

Related U.S. Application Data

(60) Provisional application No. 60/611,625, filed on Sep. 20, 2004.

(51) Int. Cl.
*A61F 5/14* (2006.01)
(52) U.S. Cl. .............. 36/140; 623/53; 36/88; 602/28
(58) Field of Classification Search ............ 623/29, 623/53–55; 36/140, 154, 88; 602/28
See application file for complete search history.

(56) References Cited

U.S. PATENT DOCUMENTS

| | | | | |
|---|---|---|---|---|
| 3,020,169 A | * | 2/1962 | Phillips, Jr. et. al. | 428/86 |
| 3,021,846 A | * | 2/1962 | Scholl | 36/154 |
| 4,463,761 A | * | 8/1984 | Pols et al. | 36/140 |
| 4,738,262 A | * | 4/1988 | Zebrack | 36/140 |
| 5,226,245 A | * | 7/1993 | Lamont | 36/9 R |
| 5,761,834 A | * | 6/1998 | Grim et al. | 36/88 |
| 5,778,563 A | * | 7/1998 | Ahlbaumer | 36/88 |
| 6,083,185 A | * | 7/2000 | Lamont | 602/65 |
| 6,102,881 A | * | 8/2000 | Quackenbush et al. | 602/28 |
| 6,594,922 B1 | * | 7/2003 | Mansfield et al. | 36/145 |
| 6,976,972 B2 | * | 12/2005 | Bradshaw | 602/23 |
| 2001/0025437 A1 | * | 10/2001 | Rork et al. | 36/88 |
| 2004/0068891 A1 | * | 4/2004 | Wang | 36/27 |
| 2006/0015050 A1 | * | 1/2006 | Bleau | 602/28 |

* cited by examiner

*Primary Examiner*—Bruce E Snow
*Assistant Examiner*—Melissa Montano
(74) *Attorney, Agent, or Firm*—Stoneman Volk Patent Group; Martin L. Stoneman; Michael D. Volk, Jr.

(57) ABSTRACT

The present invention provides improved pedorthic systems for patients having partial foot amputations or foot neuropathies. Custom-molded, custom-made pedorthics with leather linings and molded stiffeners are disclosed, along with methods of manufacture. Custom-molded, custom-made pedorthics and ankle-foot orthoses having solid, molded fillers to replace the volume of missing foot portions are also provided, along with methods of manufacture.

24 Claims, 16 Drawing Sheets

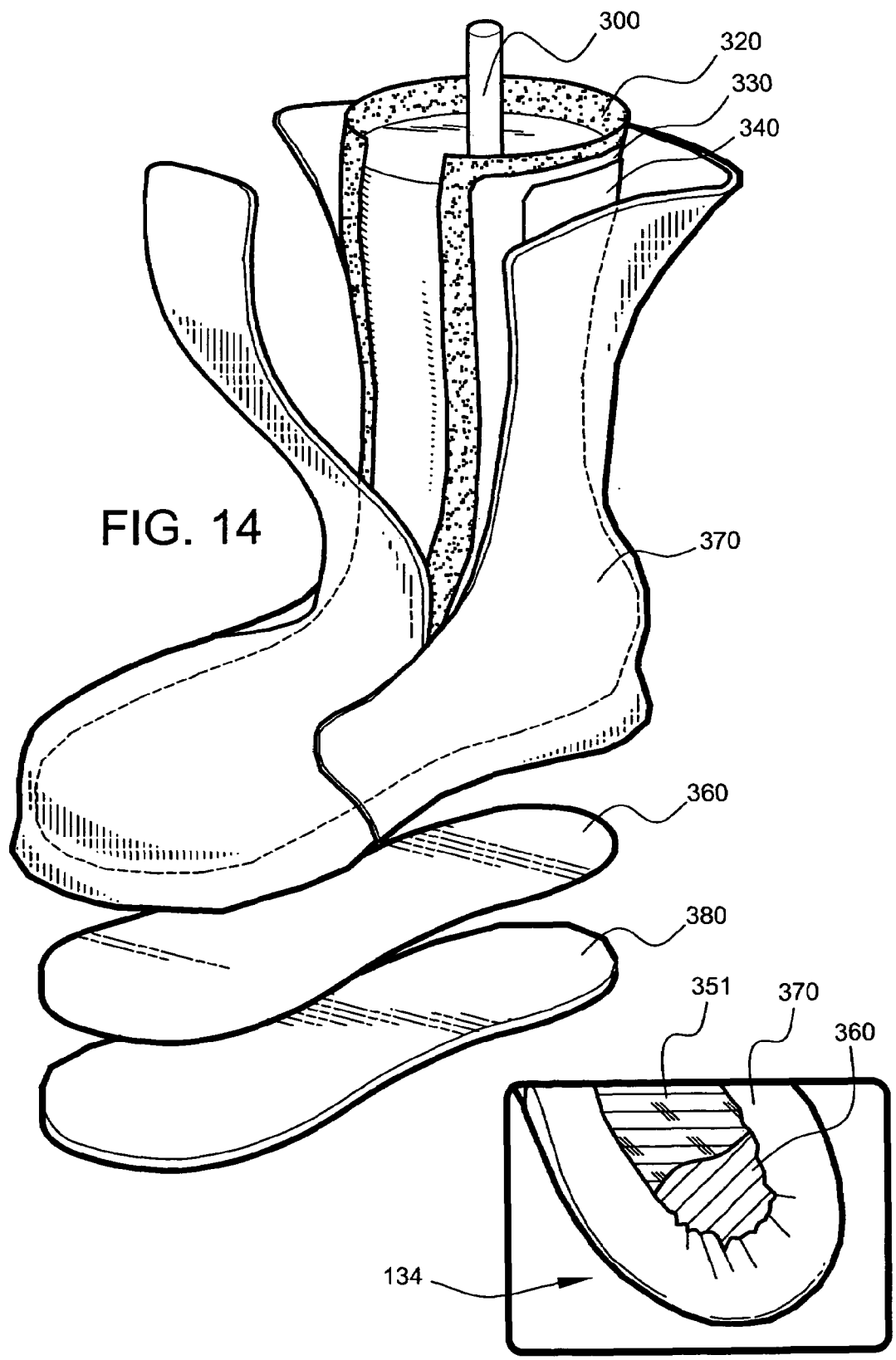

PEDORTHIC SYSTEMS

CROSS-REFERENCE TO RELATED APPLICATION

The present application is related to and claims priority from application Ser. No. 60/611,625, filed Sep. 20, 2004, entitled "PEDORTHIC SYSTEMS", the contents of which are incorporated herein by this reference and are not admitted to be prior art with respect to the present invention by the mention in this cross-reference section.

BACKGROUND

This invention relates to providing pedorthic systems. More particularly, this invention relates to providing ankle-immobilizing pedorthic systems custom-made to fit the foot of at least one patient.

Typically; persons with partial-foot amputations, foot neuropathies, and some foot deformities require prosthetics, pedorthics, and/or braces in order to walk. Typical braces are unattractive and uncomfortable.

No system exists that provides pedorthics that are attractive, comfortable, provide enhanced assistance for walking, and are durable.

Therefore, a need exists for a system of pedorthics that are attractive, comfortable, provide enhanced assistance for walking, and are durable.

OBJECTS AND FEATURES OF THE INVENTION

A primary object and feature of this invention is to overcome the above-mentioned problems and meet the above-mentioned needs. Another primary object and feature of the present invention is to provide pedorthic systems. Another primary object and feature of the present invention is to provide pedorthic systems manufacturing methods.

Another primary object and feature of the present invention is to provide an improved method of manufacturing pedorthics containing filler-portions to functionally and cosmetically replace missing foot portions. Another primary object and feature of the present invention is to provide an improved method of manufacturing pedorthics with solid, non-laminated filler portions encased within the structure of a pedorthic.

It a further object and feature of the present invention to provide such a pedorthic system having improved energy-return at toe-off to assist walking function. Another object and feature of this invention is to provide a pedorthic system with sufficient rigidity and balance to assist walking in patients without foot/ankle muscle control.

A further primary object and feature of the present invention is to provide such a system that is efficient, inexpensive, and handy. Other objects and features of this invention will become apparent with reference to the following descriptions.

SUMMARY OF THE INVENTION

In accordance with a preferred embodiment hereof, this invention provides a pedorthic system, relating to at least one pedorthic adapted to assist at least one patient requiring lower limb immobilization in order to walk, comprising: insole means for supporting to at least one lower limb in such at least one pedorthic; inner lining means for inner lining such at least one pedorthic, wherein such inner lining means substantially surrounds at least such insole means and the lower limb; wherein such inner lining means substantially surrounds at least such insole means and the lower limb; padding means for padding such at least one pedorthic, wherein said padding means substantially surrounds said inner lining means; stiffener means for stiffly supporting the lower limb in such at least one pedorthic; wherein such stiffener means substantially surrounds such padding means, and wherein such stiffener means extends forward substantially to the toe-end of such at least one pedorthic along the bottom of such at least one pedorthic; balancer means for balancing such at least one pedorthic, wherein such balancer means substantially underlies such stiffener means on the bottom of such at least one pedorthic; spring means for springing such at least one pedorthic, wherein such spring means substantially underlies such balancer means; outer lining means for outer lining such at least one pedorthic, wherein such outer lining means substantially covers the exterior surface of such at least one pedorthic; and closure means for closing such at least one pedorthic.

Moreover, it provides such a pedorthic support system, further comprising resilient unitary filler means for filling at least one void exterior to such inner lining means, and for molding to the shape of such exterior of such inner lining means. Additionally, it provides such a pedorthic support system, further comprising sole means for soling such at least one pedorthic, wherein such sole means substantially underlies such spring means on the bottom of such at least one pedorthic. Also, it provides such a pedorthic support system, further comprising midsole means for mid-soling such at least one pedorthic, wherein such midsole means substantially underlies such spring means on the bottom of such at least one pedorthic, and wherein such sole means substantially underlies such midsole means.

In accordance with another preferred embodiment hereof, this invention provides a pedorthic support system, relating to at least one pedorthic adapted to assist at least one patient requiring lower limb immobilization in order to walk, comprising: insole means for supporting to at least one lower limb in such at least one pedorthic, wherein such insole means comprises custom-molded insole means for custom-molding at least one resilient liner to the shape of the bottom of such at least one patient's lower limb; inner lining means for inner lining such at least one pedorthic wherein such inner lining means substantially surrounds at least such insole means and at least one portion of such at least one patient's lower limb, and wherein such inner lining means is custom shaped to fit around at least such insole means and at least one portion of such at least one patient's lower limb; padding means for padding such at least one pedorthic, wherein such padding means substantially surrounds such inner lining means; stiffener means for stiffly supporting the lower limb in such at least one pedorthic; wherein such stiffener means substantially surrounds such padding means, wherein such stiffener means is custom-molded to the shape of the underlying layers, and wherein such stiffener means extends forward substantially to the toe-end of such at least one pedorthic along the bottom of such at least one pedorthic; balancer means for balancing such at least one pedorthic, wherein such balancer means substantially underlies such stiffener means on the bottom of such at least one pedorthic; spring means for springing such at least one pedorthic, wherein such spring means substantially underlies such balancer means; outer lining means for outer lining such at least one pedorthic, wherein such outer lining means substantially covers the exterior surface of such at least one pedorthic; and closure means for closing such at least one pedorthic.

In addition, it provides such a pedorthic support system, further comprising resilient, unitary filler means for filling at least one void exterior to such inner lining means, and for molding to the shape of such exterior of such inner lining means. And, it provides such a pedorthic support system, further comprising sole means for soling such at least one pedorthic, wherein such sole means substantially underlies such outer lining means and such spring means on the bottom of such at least one pedorthic. Further, it provides such a pedorthic support system, further comprising midsole means for mid-soling such at least one pedorthic, wherein such midsole means substantially underlies such spring means on the bottom of such at least one pedorthic, and wherein such sole means substantially underlies such midsole means.

In accordance with another preferred embodiment hereof, this invention provides a pedorthic support system, relating to at least one pedorthic adapted to assist at least one patient requiring lower limb immobilization in order to walk, comprising: insole means for supporting to at least one lower limb in such at least one pedorthic, wherein such insole means is custom-molded to the shape of the bottom of such at least one patient's lower limb; inner lining means for inner lining such at least one pedorthic wherein such inner lining means substantially surrounds at least such insole means and at least one portion of such at least one patient's lower limb, and wherein such inner lining means is custom shaped to fit around at least such insole means and at least one portion of such at least one patient's lower limb; padding means for padding such at least one pedorthic, wherein such padding means substantially surrounds such inner lining means; stiffener means for stiffly supporting the lower limb in such at least one pedorthic; wherein such stiffener means substantially surrounds such padding means, wherein such stiffener means is custom-molded to the shape of the underlying layers, and wherein such stiffener means extends forward substantially to the toe-end of such at least one pedorthic along the bottom of such at least one pedorthic; balancer means for balancing such at least one pedorthic, wherein such balancer means substantially underlies such stiffener means on the bottom of such at least one pedorthic; spring means for springing such at least one pedorthic, wherein such spring means substantially underlies such balancer means; outer lining means for outer lining such at least one pedorthic, wherein such outer lining means substantially covers the exterior surface of such at least one pedorthic; sole means for soling such at least one pedorthic, wherein such sole means substantially underlies such spring means on the bottom of such at least one pedorthic; and closure means for closing such at least one pedorthic.

In accordance with another preferred embodiment hereof, this invention provides a pedorthic support system, relating to at least one pedorthic adapted to assist at least one patient requiring lower limb immobilization in order to walk, comprising: insole means for supporting to at least one lower limb in such at least one pedorthic, wherein such insole means is custom-molded to the shape of the bottom of such at least one patient's lower limb; inner lining means for inner lining such at least one pedorthic wherein such inner lining means substantially surrounds at least such insole means and at least one portion of such at least one patient's lower limb, and wherein such inner lining means is custom shaped to fit around at least such insole means and at least one portion of such at least one patient's lower limb; padding means for padding such at least one pedorthic, wherein such padding means substantially surrounds such inner lining means; stiffener means for stiffly supporting the lower limb in such at least one pedorthic wherein such stiffener means substantially surrounds such padding means, wherein such stiffener means is custom-molded to the shape of the underlying layers, wherein such stiffener means extends forward substantially to the toe-end of such at least one pedorthic along the bottom of such at least one pedorthic, and wherein such stiffener extends upward at least to the top edge of such insole means at the toe-end of such at least one pedorthic; balancer means for balancing such at least one pedorthic, wherein such balancer means substantially underlies such stiffener means on the bottom of such at least one pedorthic; spring means for springing such at least one pedorthic, wherein such spring means substantially underlies such balancer means; and outer lining means for outer lining such at least one pedorthic, wherein such outer lining means substantially covers the exterior surface of such at least one pedorthic; sole means for soling such at least one pedorthic, wherein such sole means substantially underlies such spring means on the bottom of such at least one pedorthic; and closure means for closing such at least one pedorthic; wherein such at least one pedorthic is substantially open over such at least one patient's toes.

In accordance with another preferred embodiment hereof, this invention provides a pedorthic support system, relating to at least one pedorthic adapted to assist at least one patient requiring lower limb immobilization in order to walk, comprising: insole means for supporting to at least one lower limb in such at least one pedorthic, wherein such insole means is custom-molded to the shape of the bottom of such at least one patient's lower limb; inner lining means for inner lining such at least one pedorthic wherein such inner lining means substantially surrounds at least such insole means and at least one portion of such at least one patient's lower limb, and wherein such inner lining means is custom shaped to fit around at least such insole means and at least one portion of such at least one patient's lower limb; resilient unitary filler means for filling at least one void exterior to such inner lining means, and for molding to the shape of such exterior of such inner lining means; padding means for padding such at least one pedorthic, wherein such padding means substantially surrounds at least such inner lining means; stiffener means for stiffly supporting the lower limb in such at least one pedorthic wherein such stiffener means substantially surrounds such padding means, wherein such stiffener means is custom-molded to the shape of the underlying layers, and wherein such stiffener means extends forward substantially to the toe-end of such at least one pedorthic along the bottom of such at least one pedorthic; balancer means for balancing such at least one pedorthic, wherein such balancer means substantially underlies such stiffener means on the bottom of such at least one pedorthic; spring means for springing such at least one pedorthic, wherein such spring means substantially underlies such balancer means; outer lining means for outer lining such at least one pedorthic, wherein such outer lining means substantially covers the exterior surface of such at least one pedorthic; sole means for soling such at least one pedorthic, wherein such sole means substantially underlies such spring means on the bottom of such at least one pedorthic; and closure means for closing such at least one pedorthic.

In accordance with another preferred embodiment hereof, this invention provides a pedorthic support system, relating to at least one pedorthic adapted to assist at least one patient requiring lower limb immobilization in order to walk, comprising: insole means for supporting to at least one lower limb in such at least one pedorthic, wherein such insole means is custom-molded to the shape of the bottom of such at least one patient's lower limb; inner lining means for inner lining such at least one pedorthic wherein such inner lining means substantially surrounds at least such insole means and at least one portion of such at least one patient's lower limb, and wherein such inner lining means is custom shaped to fit around at least such insole means and at least one portion of such at least one patient's lower limb; resilient unitary filler means for filling at least one void exterior to such inner lining means, and for molding to the shape of such exterior of such inner lining means; padding means for padding such at least one pedorthic, wherein such padding means substantially surrounds such inner lining means; stiffener means for stiffly supporting the lower limb in such at least one pedorthic wherein such stiffener means substantially surrounds such padding means, wherein such stiffener means is custom-molded to the shape of the underlying layers, and wherein such stiffener means extends forward substantially to the toe-end of such at least one pedorthic along the bottom of such at least one pedorthic; balancer means for balancing such at least one pedorthic, wherein such balancer means substantially underlies such stiffener means on the bottom of such at least one pedorthic; spring means for springing such at least one pedorthic, wherein such spring means substantially underlies such balancer means; outer lining means for outer lining such at least one pedorthic, wherein such outer lining means substantially covers the exterior surface of such at least one pedorthic; sole means for soling such at least one pedorthic, wherein such sole means substantially underlies such spring means on the bottom of such at least one pedorthic; and closure means for closing such at least one pedorthic; wherein such at least one pedorthic is sized and shaped to fit into at least one non-custom shoe purchased by the patient.

In accordance with another preferred embodiment hereof, this invention provides a pedorthic support system, relating to at least one pedorthic adapted to assist at least one patient requiring lower limb immobilization in order to walk, comprising: at least one insole adapted to supporting to at least one lower limb in such at least one pedorthic; at least one inner lining adapted to inner lining such at least one pedorthic, wherein such at least inner lining substantially surrounds such at least one insole and at least one portion of the lower limb; at least one padding adapted to pad such at least one pedorthic, wherein such at least one padding substantially surrounds such at least one inner lining; at least one stiffener adapted to stiffly support the lower limb and the foot in such at least one pedorthic wherein such at least one stiffener substantially surrounds such at least one padding, and wherein such at least one stiffener extends forward substantially to the toe-end of such at least one pedorthic along the bottom of such at least one pedorthic; at least one balancer adapted to balancing such at least one pedorthic, wherein such at least one balancer substantially underlies such at least one stiffener on the bottom of such at least one pedorthic; at least one spring adapted to springing such at least one pedorthic, wherein such at least one spring substantially underlies such at least one balancer; at least one outer lining adapted to outer lining such at least one pedorthic, wherein such at least one outer lining substantially covers the exterior surface of such at least one pedorthic, and at least one closure adapted to close such at least one pedorthic.

Even further, it provides such a pedorthic support system, further comprising at least one resilient unitary filler adapted to fill at least one void exterior to such at least one inner lining, and for molding to the shape of such exterior of such at least one inner lining. Moreover, it provides such a pedorthic support system, further comprising at least one sole adapted to sole such at least one pedorthic, wherein such at least one sole substantially underlies such at least one spring on the bottom of such at least one pedorthic. Additionally, it provides such a pedorthic support system, further comprising at least one midsole adapted to midsole such at least one pedorthic, wherein such at least one midsole substantially underlies such at least one spring on the bottom of such at least one pedorthic, and wherein such at least one sole substantially underlies such at least one midsole.

In accordance with another preferred embodiment hereof, this invention provides a pedorthic support system, relating to at least one pedorthic adapted to assist at least one patient requiring lower limb immobilization in order to walk, comprising: at least one insole adapted to support at least one lower limb in such at least one pedorthic, wherein such at least one insole is custom-molded to the shape of the bottom of such at least one patient's lower limb; at least one inner lining adapted to inner lining such at least one pedorthic wherein such at least one inner lining substantially surrounds at least such at least one insole and at least one portion of such at least one patient's lower limb, and wherein such at least one inner lining is custom shaped to fit around at least such at least one insole and at least one portion of such at least one patient's lower limb; at least one padding adapted to padding such at least one pedorthic, wherein such at least one padding substantially surrounds such at least one inner lining; at least one stiffener adapted to stiffly support the lower limb in such at least one pedorthic wherein such at least one stiffener substantially surrounds such at least one padding, wherein such at least one stiffener is custom-molded to the shape of the underlying layers, and wherein such at least one stiffener extends forward substantially to the toe-end of such at least one pedorthic along the bottom of such at least one pedorthic; at least one balancer adapted to balance such at least one pedorthic, wherein such at least one balancer substantially underlies such at least one stiffener on the bottom of such at least one pedorthic; at least one spring adapted to spring such at least one pedorthic, wherein such at least one spring substantially underlies such at least one balancer; at least one outer lining adapted to outer lining such at least one pedorthic, wherein such at least one outer lining substantially covers the exterior surface of such at least one pedorthic; and at least one closure adapted to close such at least one pedorthic.

Also, it provides such a pedorthic support system, further comprising at least one resilient unitary filler adapted to fill at least one void exterior to such at least one inner lining, and for molding to the shape of such exterior of such at least one inner lining. In addition, it provides such a pedorthic support system, wherein such at least one resilient unitary filler comprises at least one polyurethane foam. And, it provides such a pedorthic support system, wherein such at least one resilient unitary filler comprises at least one tough, microcellular, flexible, two-component, polyurethane foam.

Further, it provides such a pedorthic support system, further comprising at least one sole adapted to sole such at least one pedorthic, wherein such at least one sole substantially underlies such at least one spring on the bottom of such at least one pedorthic. Even further, it provides such a pedorthic support system, wherein such at least one sole comprises at least one leather. Moreover, it provides such a pedorthic support system, wherein such at least one sole comprises at least one plastic. Additionally, it provides such a pedorthic support system, further comprising at least one midsole adapted to midsole such at least one pedorthic, wherein such at least one midsole substantially underlies such at least one spring on the bottom of such at least one pedorthic, and wherein such at least one sole substantially underlies such at least one midsole.

Also, it provides such a pedorthic support system, wherein such at least one insole comprises at least one thermoplastic foam. In addition, it provides such a pedorthic support system, wherein such at least one inner lining comprises at least one leather. And, it provides such a pedorthic support system, wherein such at least one padding comprises at least one thermoplastic foam. Further, it provides such a pedorthic support system, wherein such at least one stiffener comprises at least one thermoplastic. Even further, it provides such a pedorthic support system, wherein such at least one balancer comprises cork in at least one thermoplastic matrix.

Even further, it provides such a pedorthic support system, wherein such at least one spring comprises at least one carbon fiber plate. Even further, it provides such a pedorthic support system, wherein such at least one carbon fiber plate comprises Springlite Carbon Fiber Laminate. Even further, it provides such a pedorthic support system, wherein such at least one outer lining comprises at least one leather.

In accordance with another preferred embodiment hereof, this invention provides a pedorthic support system, relating to at least one pedorthic adapted to assist at least one patient requiring lower limb immobilization in order to walk, comprising: at least one insole adapted to support at least one lower limb in such at least one pedorthic, wherein such at least one insole is custom-molded to the shape of the bottom of such at least one patient's lower limb; at least one inner lining adapted to inner lining such at least one pedorthic wherein such at least one inner lining substantially surrounds at least such at least one insole and at least one portion of such at least one patient's lower limb, and wherein such at least one inner lining is custom shaped to fit around at least such at least one insole and at least one portion of such at least one patient's lower limb; at least one padding adapted to padding such at least one pedorthic, wherein such at least one padding substantially surrounds such at least one inner lining; at least one stiffener adapted to stiffly support the lower limb in such at least one pedorthic wherein such at least one stiffener substantially surrounds such at least one padding, wherein such at least one stiffener is custom-molded to the shape of the underlying layers, and wherein such at least one stiffener extends forward substantially to the toe-end of such at least one pedorthic along the bottom of such at least one pedorthic; at least one balancer adapted to balance such at least one pedorthic, wherein such at least one balancer substantially underlies such at least one stiffener on the bottom of such at least one pedorthic; at least one spring adapted to spring such at least one pedorthic, wherein such at least one spring substantially underlies such at least one balancer; at least one outer lining adapted to outer lining such at least one pedorthic, wherein such at least one outer lining substantially covers the exterior surface of such at least one pedorthic; at least one sole adapted to sole such at least one pedorthic, wherein such at least one sole substantially underlies such at least one spring on the bottom of such at least one pedorthic; and at least one closure adapted to close such at least one pedorthic.

In accordance with another preferred embodiment hereof, this invention provides a pedorthic support system, relating to at least one pedorthic adapted to assist at least one patient requiring lower limb immobilization in order to walk, comprising: at least one insole adapted to support at least one lower limb in such at least one pedorthic, wherein such at least one insole is custom-molded to the shape of the bottom of such at least one patient's lower limb; at least one inner lining adapted to inner lining such at least one pedorthic wherein such at least one inner lining substantially surrounds at least such at least one insole and at least one portion of such at least one patient's lower limb, and wherein such at least one inner lining is custom shaped to fit around at least such at least one insole and at least one portion of such at least one patient's lower limb; at least one padding adapted to padding such at least one pedorthic, wherein such at least one padding substantially surrounds such at least one inner lining; at least one stiffener adapted to stiffly support the lower limb in such at least one pedorthic wherein such at least one stiffener substantially surrounds such at least one padding, wherein such at least one stiffener is custom-molded to the shape of the underlying layers, wherein such at least one stiffener extends forward substantially to the toe-end of such at least one pedorthic along the bottom of such at least one pedorthic, and wherein such at least one stiffener extends upward at least to the top edge of such at least one insole at the toe-end of such at least one pedorthic; at least one balancer adapted to balance such at least one pedorthic, wherein such at least one balancer substantially underlies such at least one stiffener on the bottom of such at least one pedorthic; at least one spring adapted to spring such at least one pedorthic, wherein such at least one spring substantially underlies such at least one balancer; at least one outer lining adapted to outer lining such at least one pedorthic, wherein such at least one outer lining substantially covers the exterior surface of such at least one pedorthic; at least one sole adapted to sole such at least one pedorthic, wherein such at least one sole substantially underlies such at least one spring on the bottom of such at least one pedorthic; and at least one closure adapted to close such at least one pedorthic; wherein such at least one pedorthic is substantially open over such at least one patient's toes.

In accordance with another preferred embodiment hereof, this invention provides a pedorthic support system, relating to at least one pedorthic adapted to assist at least one patient requiring lower limb immobilization in order to walk, comprising: at least one insole adapted to supporting to at least one lower limb in such at least one pedorthic, wherein such at least one insole means is custom-molded to the shape of the bottom of such at least one patient's lower limb; at least one inner lining adapted to inner lining such at least one pedorthic wherein such at least one inner lining substantially surrounds at least such at least one insole and at least one portion of such at least one patient's lower limb, and wherein such at least one inner lining is custom shaped to fit around at least such at least one insole and at least one portion of such at least one patient's lower limb; at least one resilient unitary filler adapted to fill at least one void exterior to such at least one inner lining, and for molding to the shape of such exterior of such at least one inner lining; at least one padding adapted to padding such at least one pedorthic, wherein such at least one padding substantially surrounds such at least one inner lining; at least one stiffener adapted to stiffly support the lower limb in such at least one pedorthic wherein such at least one stiffener substantially surrounds such at least one padding, wherein such at least one stiffener is custom-molded to the shape of the underlying layers, and wherein such at least one stiffener extends forward substantially to the toe-end of such at least one pedorthic along the bottom of such at least one pedorthic; at least one balancer adapted to balance such at least one pedorthic, wherein such at least one balancer substantially underlies such at least one stiffener on the bottom of such at least one pedorthic; at least one spring adapted to springing such at least one pedorthic, wherein such at least one spring substantially underlies such at least one balancer; at least one outer lining adapted to outer lining such at least one pedorthic, wherein such at least one outer lining substantially covers the exterior surface of such at least one pedorthic; at least one sole adapted to sole such at least one pedorthic, wherein such at least one sole substantially underlies such at least one spring on the bottom of such at least one pedorthic; and at least one closure adapted to close such at least one pedorthic.

In accordance with another preferred embodiment hereof, this invention provides a pedorthic support system, relating to at least one pedorthic adapted to assist at least one patient requiring lower limb immobilization in order to walk, comprising: at least one insole adapted to support at least one lower limb in such at least one pedorthic, wherein such at least one insole is custom-molded to the shape of the bottom of such at least one patient's lower limb; at least one inner lining adapted to inner lining such at least one pedorthic wherein such at least one inner lining substantially surrounds at least such at least one insole and at least one portion of such at least one patient's lower limb, and wherein such at least one inner lining is custom shaped to fit around at least such at least one insole and at least one portion of such at least one patient's lower limb; at least one resilient unitary filler adapted to fill at least one void exterior to such at least one inner lining, and for molding to the shape of such exterior of such at least one inner lining; at least one padding adapted to padding such at least one pedorthic, wherein such at least one padding substantially surrounds such at least one inner lining; at least one stiffener adapted to stiffly support the lower limb in such at least one pedorthic wherein such at least one stiffener substantially surrounds such at least one padding, wherein such at least one stiffener is custom-molded to the shape of the underlying layers, and wherein such at least one stiffener extends forward substantially to the toe-end of such at least one pedorthic along the bottom of such at least one pedorthic; at least one balancer adapted to balance such at least one pedorthic, wherein such at least one balancer substantially underlies such at least one stiffener on the bottom of such at least one pedorthic; at least one spring adapted to spring such at least one pedorthic, wherein such at least one spring substantially underlies such at least one balancer; at least one outer lining adapted to outer lining such at least one pedorthic, wherein such at least one outer lining substantially covers the exterior surface of such at least one pedorthic; at least one sole adapted to sole such at least one pedorthic, wherein such at least one sole substantially underlies such at least one spring on the bottom of such at least one pedorthic; and at least one closure adapted to close such at least one pedorthic; wherein such at least one pedorthic is sized and shaped to fit into at least one non-custom shoe purchased by the patient.

In accordance with another preferred embodiment hereof, this invention provides a pedorthic support system, relating to at least one pedorthic adapted to assist at least one patient requiring lower limb immobilization in order to walk, comprising the steps of: acquiring at least one positive cast of such at least one patient's lower limb; molding at least one insole to the shape of such at least one positive cast on the portion of such at least one positive cast representing the bottom of such at least one patient's lower limb; making at least one inner lining and applying such at least one inner lining over the insole and such at least one positive cast; applying at least one layer of padding at least onto substantially the entire inner lining; thermoforming at least one stiffener onto the positive cast and the prior-made layers; trimming such at least one stiffener to at least one shape permitting access to the foot and substantially surrounding the prior-made layers around the lower limb and substantially underlying the prior-made layers along the bottom of such at least one pedorthic; applying at least one balancer to the bottom of such at least one stiffener; trimming such at least one balancer to provide at least one substantially flat end balanced bottom surface; applying at least one spring plate to substantially the entire bottom of such at least one balancer; making at least one outer layer to fit substantially over all of the prior-made layers but such at least one spring plate; attaching such at least one outer layer to the prior-made layers, slightly overlapping the bottom of the spring plate; applying at least one sole extending over at least the bottom of such at least one spring plate; and applying at least one closure such at least one pedorthic.

Even further, it provides such a pedorthic support system, further comprising the step of applying at least one midsole to at least the bottom of such at least one spring plate. Even further, it provides such a pedorthic support system, further comprising the step of applying at least one raised cutting guide to such positive cast and the prior-made layers prior to thermoforming such at least one stiffener onto the positive cast and the prior-made layers. Even further, it provides such a pedorthic support system, wherein the step of trimming such at least one stiffener to the proper shape comprises the step of trimming such at least one stiffener to the proper shape, substantially surrounding the back of the lower limb, substantially underlying the bottom of the lower limb, and substantially covering the bottom and sides of such at least one insole. Even further, it provides such a pedorthic support system, further comprising the step of trimming and finishing such at least one pedorthic into an open-toe shape.

In accordance with another preferred embodiment hereof, this invention provides a pedorthic support system, relating to at least one pedorthic adapted to assist at least one patient requiring lower limb immobilization in order to walk, comprising the product made by the above process.

In accordance with another preferred embodiment hereof, this invention provides a pedorthic support system, relating to at least one pedorthic adapted to assist at least one patient requiring lower limb immobilization in order to walk, comprising the steps of: acquiring at least one positive cast of such at least one patient's lower limb; molding at least one insole to the shape of such at least one positive cast on the portion of such at least one positive cast representing the bottom of such at least one patient's lower limb; making at least one inner lining and applying such at least one inner lining over the insole and such at least one positive cast; forming at least one resilient unitary filler, adhered to at least one portion of such at least one inner lining; trimming such at least one resilient unitary filler to at least one final desired shape; applying at least one layer of padding at least onto substantially the entire inner lining; thermoforming at least one stiffener onto the positive cast and the prior-made layers; trimming such at least one stiffener to at least one shape permitting access to the foot and substantially surrounding the prior-made layers around the lower limb and substantially underlying the prior-made layers along the bottom of such at least one pedorthic; applying at least one balancer to the bottom of such at least one stiffener; trimming such at least one balancer to provide at least one substantially flat and balanced bottom surface; applying at least one spring plate to substantially the entire bottom of such at least one balancer; making at least one outer layer to fit substantially over all of the prior-made layers but such at least one spring plate; attaching such at least one outer layer to the prior-made layers, slightly overlapping the bottom of the spring plate; applying at least one sole extending over at least the bottom of such at least one spring plate; applying at least one closure to such at least one pedorthic.

Even further, it provides such a pedorthic support system, further comprising the step of applying at least one midsole to at least the bottom of such at least one spring plate. Even further, it provides such a pedorthic support system, further comprising the step of applying at least one raised cutting guide to such positive cast and the prior-made layers prior to thermoforming such at least one stiffener onto the positive cast and the prior-made layers.

In accordance with another preferred embodiment hereof, this invention provides a pedorthic support system, relating to at least one pedorthic adapted to assist at least one patient requiring lower limb immobilization in order to walk, comprising the product made by the above process.

In accordance with another preferred embodiment hereof, this invention provides a pedorthic support system, relating to at least one pedorthic adapted to assist at least one patient requiring lower limb immobilization in order to walk, comprising the steps of: preparing at least one positive cast of such at least one lower limb; preparing at least one inner lining surrounding such at least one positive cast of such at least one lower limb; preparing at least one dam, attached to such at least one inner lining, at least surrounding the volume of the missing portions of such at least one lower limb; filling such at least one dam with at least one uncured polyurethane foam; allowing such at least one polyurethane foam to cure; removing such at least one dam; shaping such at least one cured polyurethane foam to the desired shape; building at least one pedorthic onto such at least one shaped polyurethane foam and such at least one inner lining.

Even further, it provides such a pedorthic support system, wherein such step of shaping such at least one cured polyurethane foam to the desired shape comprises the step of shaping such at least one cured polyurethane foam into the shape of the missing portions of the lower limb. Even further, it provides such a pedorthic support system, wherein such step of shaping such at least one cured polyurethane foam to the desired shape comprises the step of shaping such at least one cured polyurethane foam into the shape of the inside of such at least one pedorthic of an appropriate size for the patient.

In accordance with another preferred embodiment hereof, this invention provides a pedorthic support system, relating to at least one pedorthic adapted to assist at least one patient requiring lower limb immobilization in order to walk, comprising the product made by the above process.

BRIEF DESCRIPTION OF THE DRAWINGS

FIG. 14 shows a partially exploded view illustrating the positive cast with applied inner lining, padding, trimmed stiffener, sole-plate, outer lining, and sole.

FIG. 15 shows a bottom view illustrating a completed partial-foot Ankle-Foot Orthosis ((AFO) pedorthic with the sole peeled back to reveal the sole-plate.

DETAILED DESCRIPTION OF THE BEST MODES AND PREFERRED EMBODIMENTS OF THE INVENTION

Figures 1, 2:
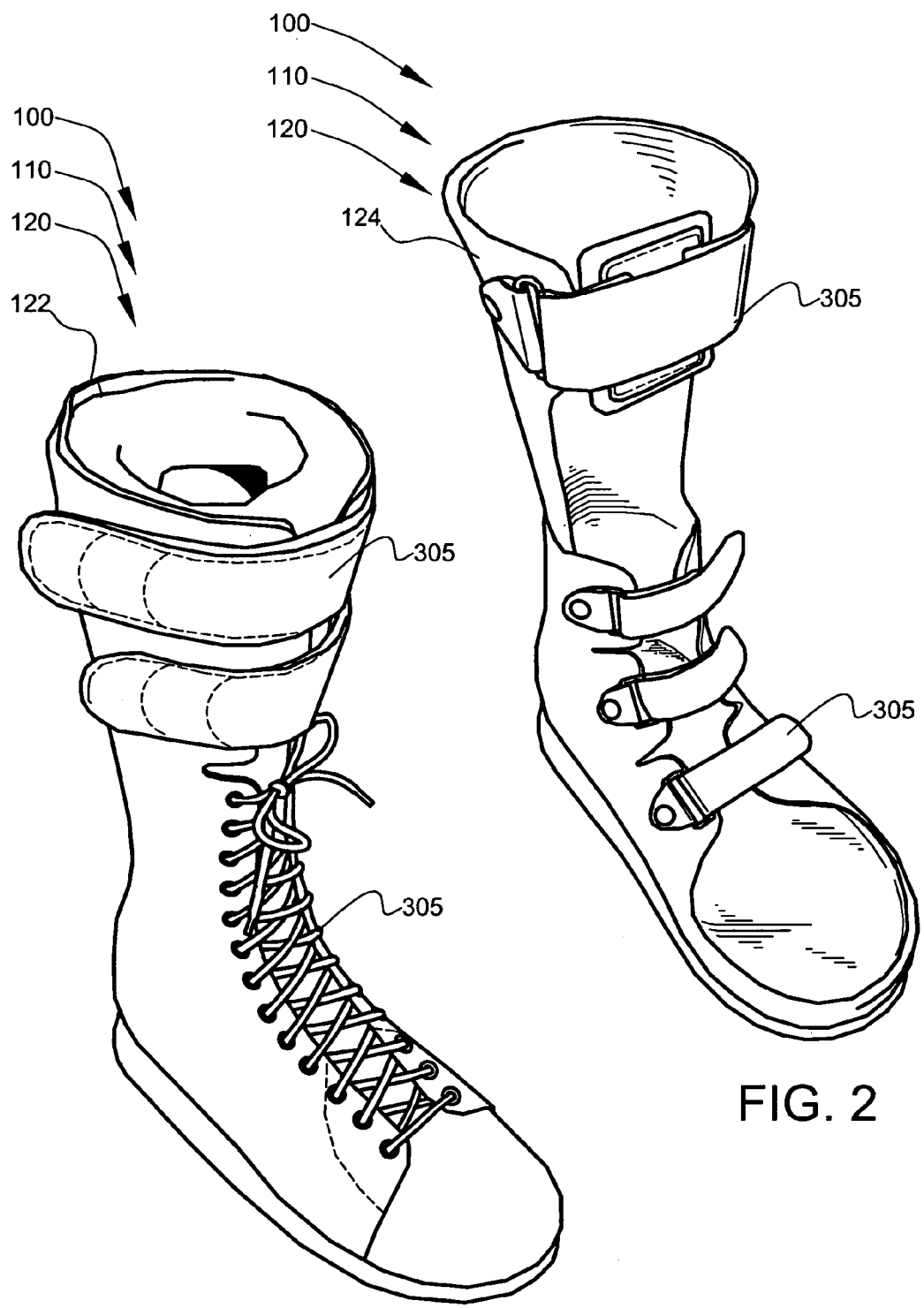
FIG. 1 shows an isometric view illustrating a neuro-walker pedorthic according to a preferred embodiment of the present invention.
FIG. 2 shows an isometric view illustrating an open-toe neuro-walker pedorthic according to a preferred embodiment of the present invention.
Figure 4:
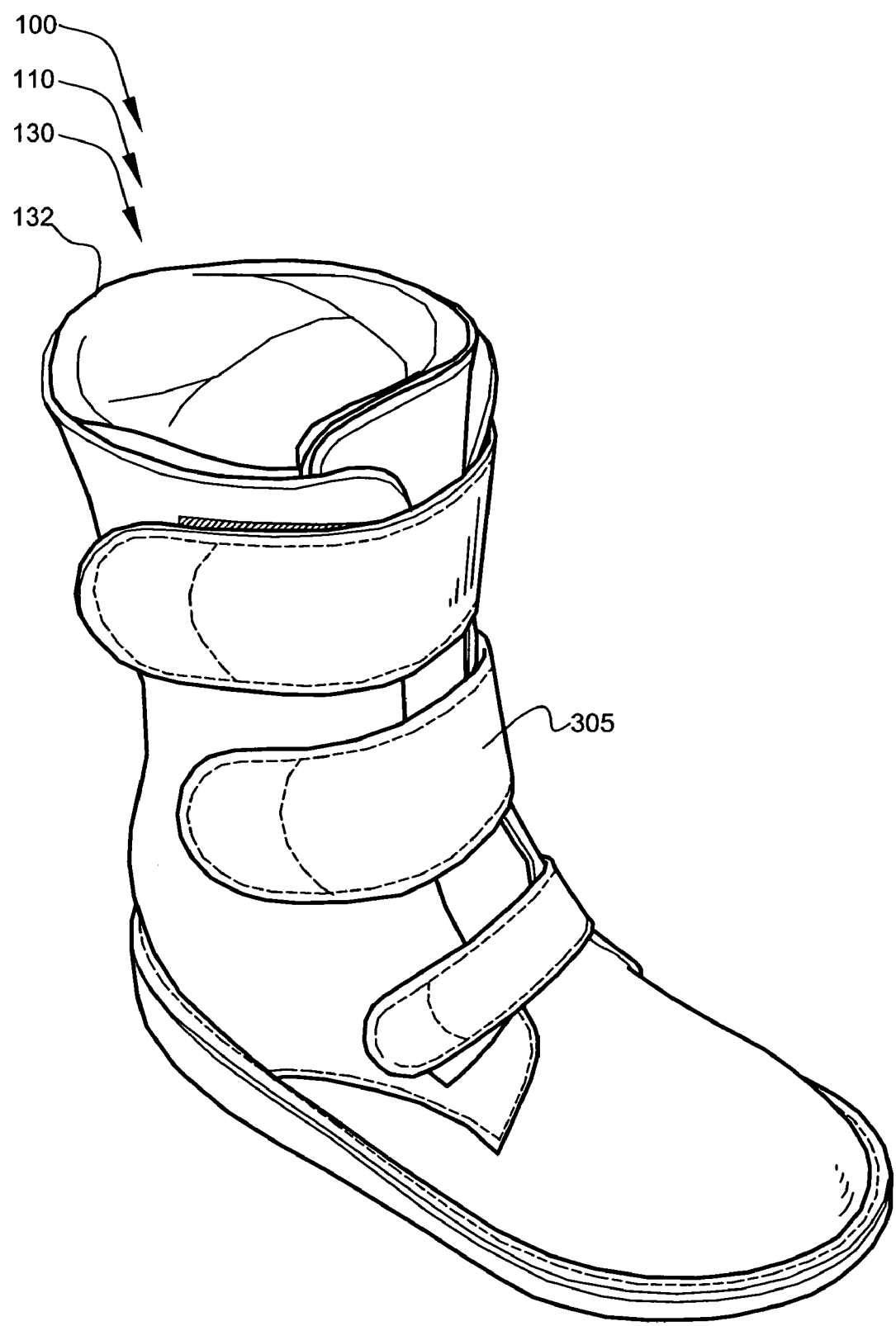
FIG. 4 shows an isometric view illustrating a partial-foot walker pedorthic according to a preferred embodiment of the present invention.
Figure 5:
FIG. 5 shows an isometric view illustrating a partial-foot Ankle-Foot Orthosis (AFO) pedorthic according to a preferred embodiment of the present invention.

FIG. 1 shows an isometric view illustrating neuro-walker pedorthic 122 according to a preferred embodiment of the present invention. FIGS. 2, 4, and 5 are photographs of related pedorthic products also referred to in this paragraph. Preferably, pedorthic system 100 comprises pedorthics 110, as shown. Preferably, pedorthics 110 comprise neuropathy pedorthic 120 and partial-foot pedorthic 130, as shown. Preferably, neuropathy pedorthic 120 comprises neuro-walker pedorthic 122, as shown. Preferably, neuropathy pedorthic 120 comprises open-toe neuro-walker pedorthic 124, as shown. Preferably, partial-foot pedorthic 130 comprises partial-foot walker pedorthic 132, as shown. Preferably, partial-foot pedorthic 130 comprises partial-foot Ankle-Foot Orthosis (AFO) pedorthic 134, as shown. Upon reading the teachings of this specification, those with ordinary skill in the art will now understand that, under appropriate circumstances, considering issues such as advances in technology, patient needs, user preference, etc., other styles, such as neuro-walker AFO, styles that extend above the knee, etc.; may suffice.

Preferably, pedorthic 110 comprises at least one shoe specially adapted enhance the function an abnormal lower limb. Preferably, the lower limb comprises the weight-bearing structures of the lower limb, usually a foot having an ankle, but commonly a partially-amputated foot, and/or a deformed foot with or without a functional ankle, and/or a lower leg without a foot.

Preferably, neuro-walker pedorthics 120 comprise at least one custom-made pedorthic boot or shoe providing complete ankle and/or lower limb immobilization and complete foot immobilization for patients with damaged motor-control of the foot and/or ankle.

FIG. 2 shows an isometric view illustrating open-toe neuro-walker pedorthic 124 according to a preferred embodiment of the present invention. Preferably, open-toe neuro-walker pedorthic 124 comprises at least one custom-made pedorthic sandal-type boot or shoe, as shown, preferably providing complete ankle immobilization and complete foot immobilization for patients with damaged motor-control of the foot and/or ankle.

Preferably, pedorthics 110 comprises closures 305, as shown. Preferably, closure 305 comprises hook-and-loop fasteners, preferably Velcro, as shown in FIG. 1. Preferably, closures 305 comprise laces, as shown in FIG. 1. Preferably, closures 305 comprise buckles, as shown in FIG. 2. Upon reading the teachings of this specification, those with ordinary skill in the art will now understand that, under appropriate circumstances, considering such issues as advances in technology, user preference, etc., other closures, such as snaps, zippers, adhesive, etc., may suffice.

Figure 3:
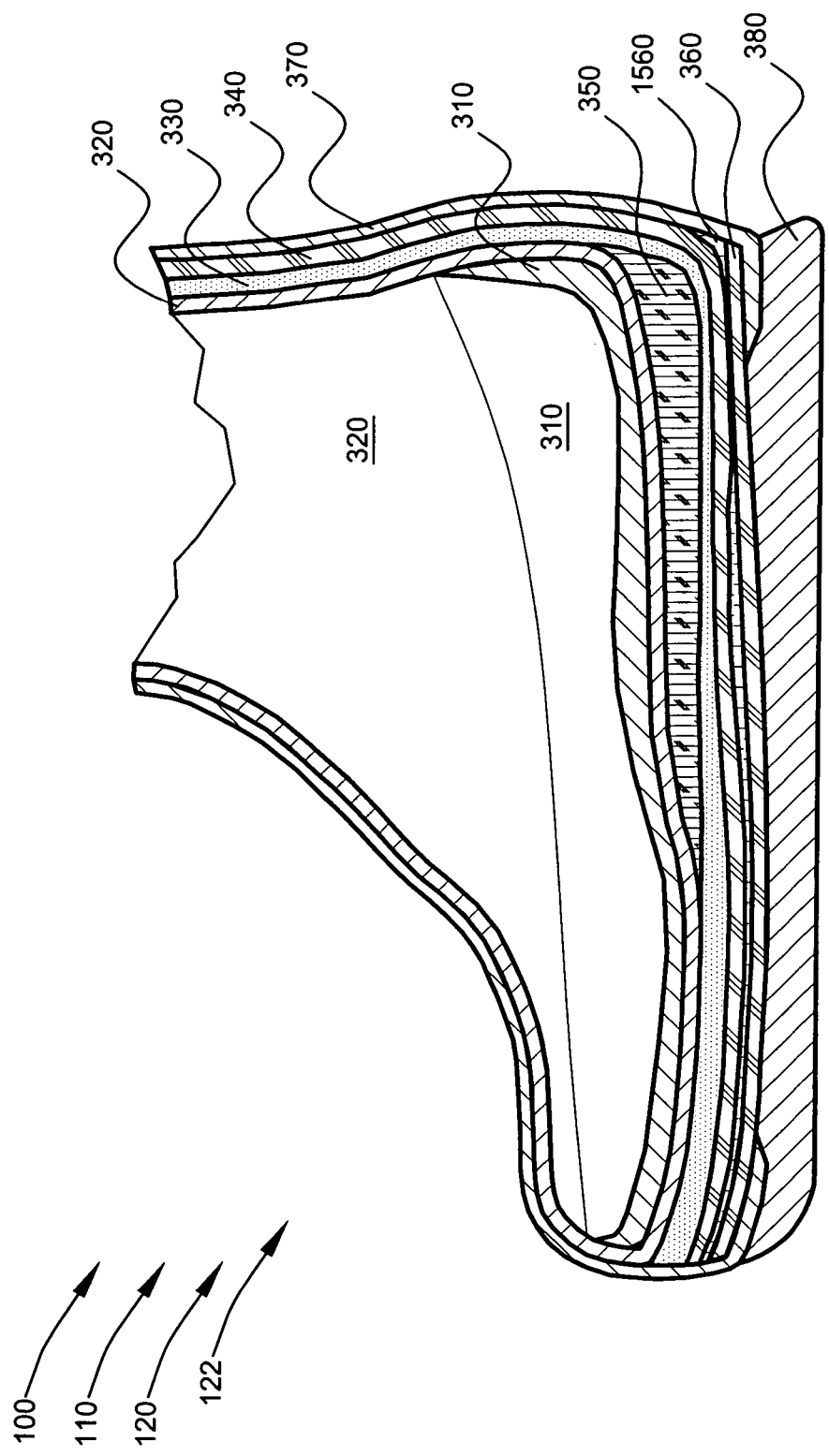
FIG. 3 shows a cross-sectional diagram illustrating the midline of the neuro-walker pedorthic according to FIG. 1.
Figure 7A:
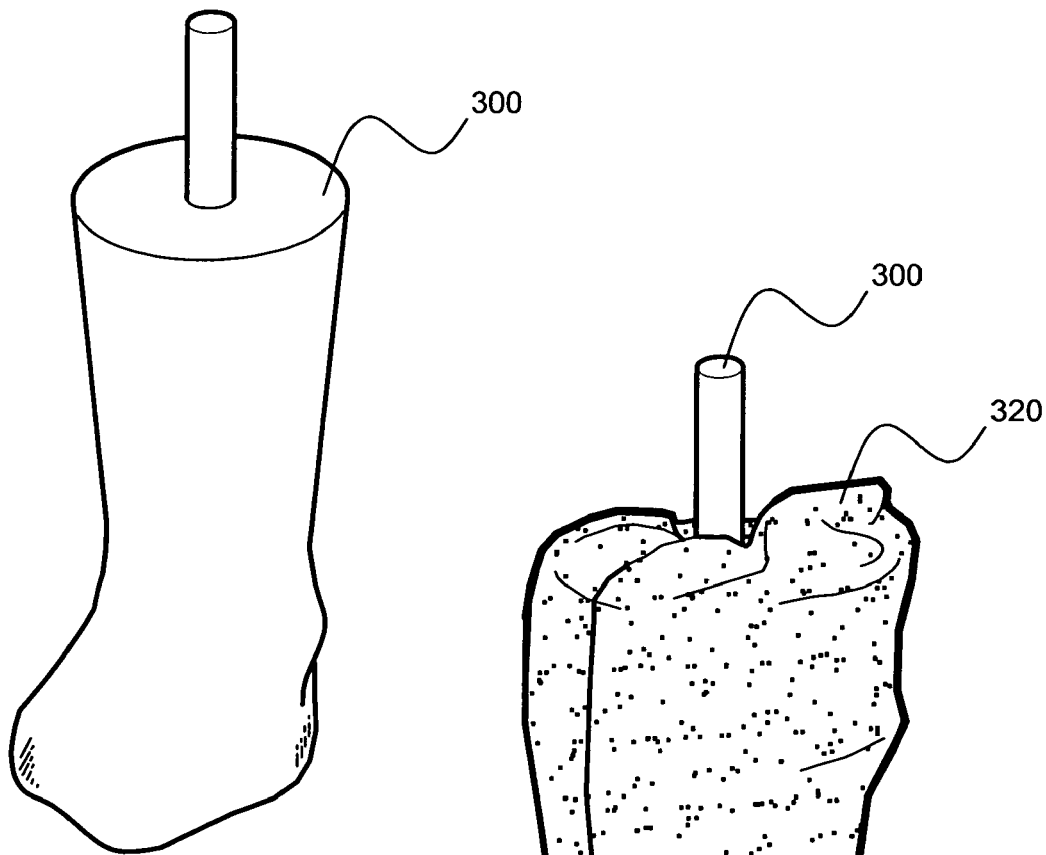
FIG. 7A shows an isometric view illustrating a partial-foot positive cast.

FIG. 3 shows a cross-sectional diagram illustrating the midline of neuro-walker pedorthic 122 according to FIG. 1. Preferably, pedorthics 110 are custom made using positive cast 300 of a patient's foot, as shown in FIG. 7A. Preferably, the inner layers of pedorthic 110 are made first, then the next most outer layer, etc., with the outermost layer completed last. Preferably, most construction steps are done on positive cast 300 (see FIG. 7A et seq.). Preferably, positive cast 300 comprises a life-sized replica of a patient's lower limb, preferably a positive plaster cast, as shown in FIG. 7A. Upon reading the teachings of this specification, those with ordinary skill in the art will now understand that, under appropriate circumstances, considering issues such as advances in technology, patent needs, user preference, etc., other arrangements may suffice, such as assembling layers in other orders, other types of patient limb replicas, such as a custom-made last, a machine-made replica made using laser-scanned contour data of the lower limb, an off-the shelf last that is an excellent shape match, etc., may suffice.

Figure 7B:
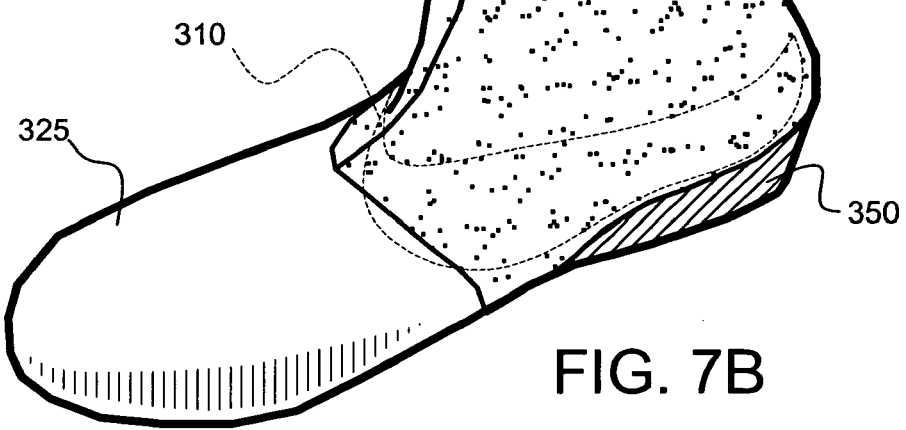
FIG. 7B shows an isometric view illustrating the partial-foot positive cast having applied insole, inner lining, balancer, and completed toe-filler.

Preferably, with reference to FIG. 3, insole 310 is first molded onto positive cast 300. Preferably, insole 310 comprises thermoplastic foam material. Then, inner lining 320 (which is preferably leather) is fitted and sewn over positive cast 300 and insole 310, as shown in FIG. 7B. Next, balancer 350 is applied to the bottom of inner lining 320 to provide heel and arch support and a balanced and flat-bottomed walking surface, as shown. Preferably, balancer 350 comprises thermoplastic cork material. Next, padding 330 is applied over inner lining 320, balancer 350, and insole 310, preferably using one-quarter-inch thick thermoplastic foam, as shown. Then, stiffener 340 is molded over padding 330, inner lining 320, balancer 350, and insole 310. Preferably, stiffener 340 comprises strong thermoplastic sheet material, as shown. Then, sole plate 360 is applied or molded to the bottom of stiffener 340, as shown, to provide springy energy-return on toe-off while walking. Preferably, sole plate 360 comprises thermoplastic carbon-fiber plate. Preferably, if needed, an additional balance layer 1560 comprising thermoplastic cork is applied to flatten the interface between stiffener 340 and sole plate 360, as shown. Next, outer lining 370 is glued and sewn to inner lining 320 and to the other prior-made layers, as shown. Finally, sole 380 is applied to the bottom of neuro-walker pedorthic 122, as shown. Upon reading the teachings of this specification, those with ordinary skill in the art will now understand that, under appropriate circumstances, considering issues such as advances in technology, patient needs, user preference, etc., other layers, such as multiple insoles, multiple linings, multiple stiffeners, multiple paddings, multiple sole plates, multiple balancers, multiple sole layers, other layers, etc., may suffice.

Figure 16:
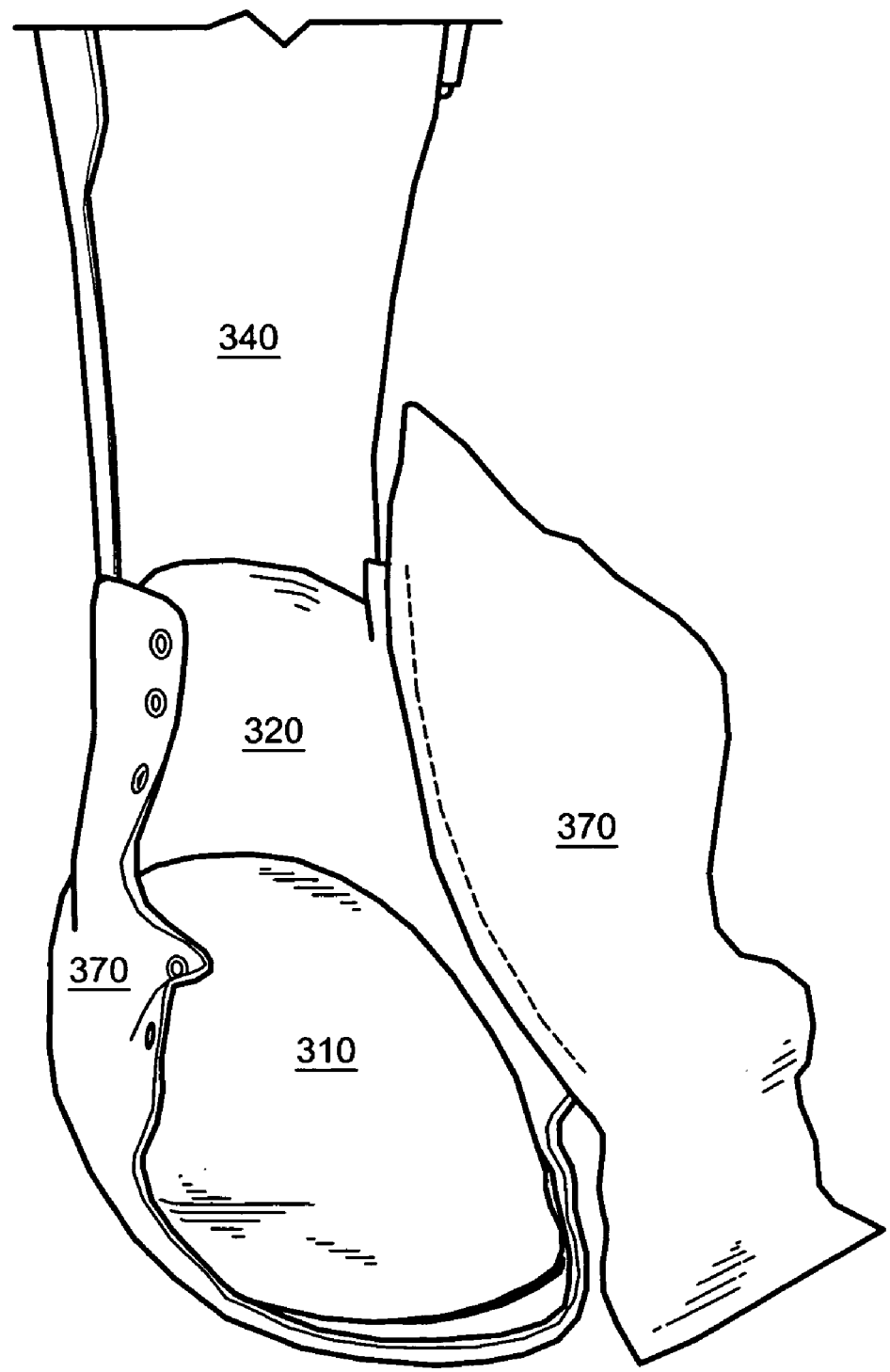
FIG. 16 shows a front view illustrating a nearly-completed neuro-walker pedorthic, showing the removable insole.

The construction and cross-section of open-toe neuro-walker pedorthic 124 (at least embodying herein wherein such at least one pedorthic is substantially open over such at least one patient's toes) is substantially identical, except that the inner lining 320 and outer lining 370 are trimmed and sewn into a sandal-shape, as shown in FIG. 2. Also, instead of ending at the toe as stiffener 340 does in neuro-walker pedorthic 122, in open-toe neuro-walker pedorthic 124 stiffener 340 extends upward to the top edge of insole 310 all around insole 310, to provide a secure cup to hold insole 310, as shown in FIG. 16. Upon reading the teachings of this specification, those with ordinary skill in the art will now understand that, under appropriate circumstances, considering issues such as advances in technology, patient needs, user preference, etc., other layers, such as multiple insoles, multiple linings, multiple stiffeners, multiple paddings, multiple sole plates, multiple balancers, other layers, fewer layers, other means of securing the insole, etc., may suffice.

FIG. 4 shows an isometric view illustrating partial-foot walker pedorthic 132 according to a preferred embodiment of the present invention. Preferably, partial-foot walker pedorthic 132 comprises at least one custom-made pedorthic boot or shoe, as shown, preferably providing complete lower limb immobilization and walking assistance for patients with an abnormally shaped lower limb, such as, preferably, at least one partial foot (whether the partial foot is caused by amputation or deformity).

FIG. 5 shows an isometric view illustrating partial-foot Ankle-Foot Orthosis (AFO) pedorthic 134 according to a preferred embodiment of the present invention. Preferably, partial-foot AFO pedorthic 134 comprises at least one custom-made pedorthic AFO (sized to fit in at least one normal shoe of the appropriate for the patient) providing complete lower limb immobilization and walking assistance, as shown, preferably for patients with an abnormally shaped lower limb, preferably at least one partial foot (whether the partial foot is caused by amputation or deformity).

Figure 6:
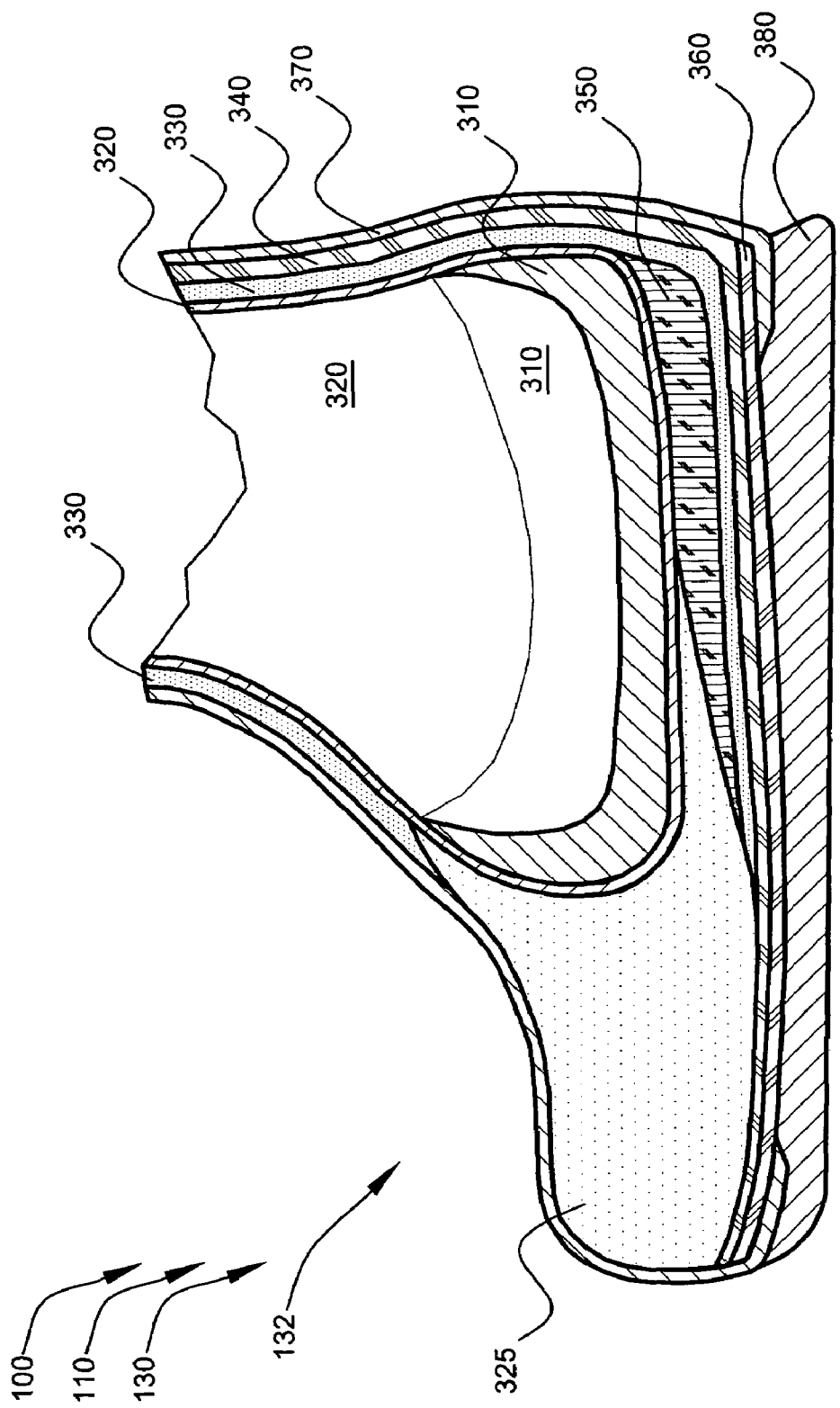
FIG. 6 shows a cross-sectional diagram illustrating the midline of the partial-foot walker pedorthic according to FIG. 4.

FIG. 6 shows a cross-sectional diagram illustrating through the midline of partial-foot walker pedorthic 132 according to FIG. 4. Preferably, the construction of partial-foot pedorthic 130 is similar to the construction of neuropathy pedorthic 120, as shown. Preferably, most construction steps are done on positive cast 300.

Preferably, insole 310 (at least embodying herein at least one insole adapted to supporting to at least one-lower limb in such at least one pedorthic) is first molded onto positive cast 300. Preferably, insole 310 comprises thick thermoplastic foam material. Preferably, insole 310 comprises about one-half inch thick Plastazote™ polyethylene foam, as shown. Upon reading the teachings of this specification, those with ordinary skill in the art will now understand that, under appropriate circumstances, considering such issues as advances in technology, user preference, etc., other padding materials, such as memory foam, polyurethane, neoprene, rubber, etc., may suffice.

Then, inner lining 320 (at least embodying herein wherein such inner lining means substantially surrounds at least such insole means and the lower limb, and at least embodying herein at least one inner lining adapted to inner lining such at least one pedorthic) is fitted and applied over positive cast 300 and insole 310, as shown (see FIG. 7B). Preferably, inner lining 320 comprises leather, as shown. Upon reading the teachings of this specification, those with ordinary skill in the art will now understand that, under appropriate circumstances, considering issues such as advances in technology, user preference, etc., other outer lining materials, such as fabric, vinyl, neoprene, etc., may suffice.

Figure 8:
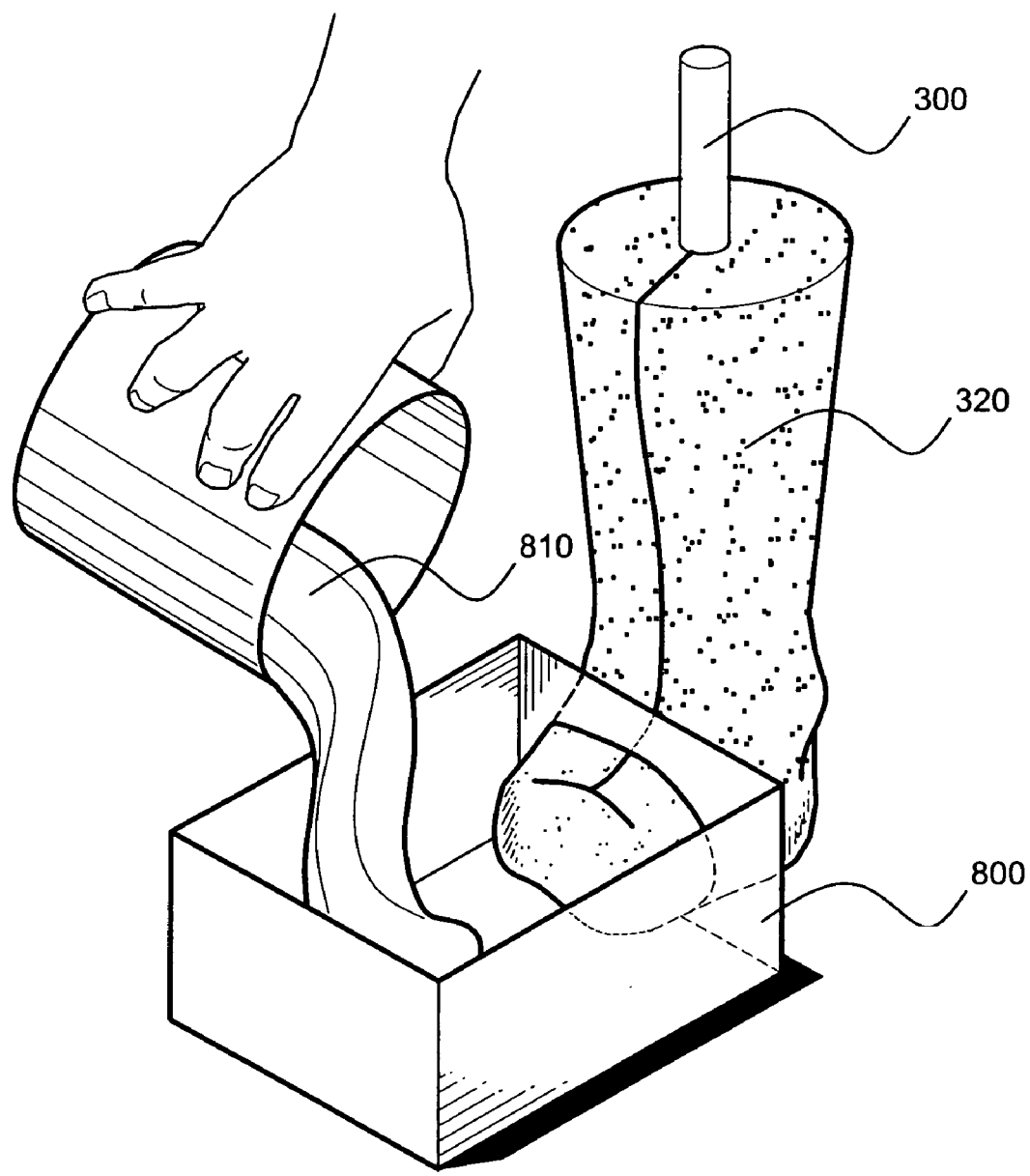
FIG. 8 shows a diagram of the method of forming the toe-filler on the positive cast with the insole and inner lining.

Then, toe-filler 325 is applied to inner lining 320, as shown and further described in FIG. 8.

Next, balancer 350 (at least embodying herein balancer means for balancing such at least one pedorthic, wherein such balancer means substantially underlies such stiffener means on the bottom of such at least one pedorthic; and at least embodying herein at least one balancer adapted to balancing such at least one pedorthic, wherein such at least one balancer substantially underlies such at least one stiffener on the bottom of such at least one pedorthic) is applied to the bottom of inner lining 320, preferably using thermoplastic cork material to provide heel and arch support and a balanced and flat-bottomed walking surface, as shown.

Next, padding 330 (at least embodying herein padding means for padding such at least one pedorthic, wherein said padding means substantially surrounds said inner lining means; and at least embodying herein at least one padding adapted to pad such at least one pedorthic, wherein such at least one padding substantially surrounds such at least one inner lining) is molded over inner lining 320, toe-filler 325, balancer 350, and insole 310 (see FIG. 10), as shown. Preferably, padding 330 comprises thin thermoplastic foam, as shown. Preferably, padding 330 comprises about one-quarter inch thick Plastazote™ polyethylene foam, as shown. Upon reading the teachings of this specification, those with ordinary skill in the art will now understand that, under appropriate circumstances, considering such issues as advances in technology, user preference, etc., other padding materials, such as memory foam, polyurethane, neoprene, rubber, etc., may suffice.

Then, stiffener 340 (at least embodying herein stiffener means for stiffly supporting the lower limb in such at least one pedorthic, wherein such stiffener means substantially surrounds such padding means, and wherein such stiffener means extends forward substantially to the toe-end of such at least one pedorthic along the bottom of such at least one pedorthic; and at least embodying herein at least one stiffener adapted to stiffly support the lower limb and the foot in such at least one pedorthic wherein such at least one stiffener substantially surrounds such at least one padding, and wherein such at least one stiffener extends forward substantially to the toe-end of such at least one pedorthic along the bottom of such at least one pedorthic) is molded (see FIG. 12) over padding 330, toe-filler 325, inner lining 320, balancer 350, and insole 310, as shown. Preferably, stiffener 340 comprises strong thermoplastic sheet material, as shown. Preferably, stiffener 340 comprises polyethylene sheet material between about one and about five millimeters thick, as shown. Upon reading the teachings of this specification, those with ordinary skill in the art will now understand that, under appropriate circumstances, considering such issues as advances in technology, user preference, etc., other thermoplastics, such as acrylic, polypropylene, composite materials, carbon-fiber composites, etc., may suffice.

Then, sole plate 360 (at least embodying herein spring means for springing such at least one pedorthic, wherein such spring means substantially underlies such balancer means; and at least embodying herein at least one spring adapted to springing such at least one pedorthic, wherein such at least one spring substantially underlies such at least one balancer), is applied, as shown, to provide a springy energy-return on toe-off. Preferably, sole-plate 360 comprises thermoplastic carbon-fiber plate. Upon reading the teachings of this specification, those with ordinary skill in the art will now understand that, under appropriate circumstances, considering such issues as advances in technology, user preference, medical requirements, etc., other sole-plate materials, such as acrylic, polypropylene, thermoplastic fiberglass composites, etc., may suffice.

Next, outer lining 370 (at least embodying herein outer lining means for outer lining such at least one pedorthic, wherein such outer lining means substantially covers the exterior surface of such at least one pedorthic; and at least embodying herein at least one outer lining adapted to outer lining such at least one pedorthic, wherein such at least one outer lining substantially covers the exterior surface of such at least one pedorthic) is glued and sewn (see FIGS. 15 and 18) to inner lining 320 and the other layers, as shown. Preferably, outer lining 370 comprises leather. Upon reading the teachings of this specification, those with ordinary skill in the art will now understand that, under appropriate circumstances, considering such issues as advances in technology, user preference, etc., other outer lining materials, such as fabric, vinyl, neoprene, etc., may suffice.

Finally, sole 380 (at least embodying herein at least one sole adapted to sole such at least one pedorthic, wherein such at least one sole substantially underlies such at least one spring on the bottom of such at least one pedorthic; and at least embodying herein sole means for soling such at least one pedorthic, wherein such sole means substantially underlies such spring means on the bottom of such at least one pedorthic), which is preferably at least one durable shock-absorbing plastic material, is applied to the bottom of partial-foot walker pedorthic 132, as shown (see FIG. 14). Upon reading the teachings of this specification, those with ordinary skill in the art will now understand that, under appropriate circumstances, considering issues such as advances in technology, patient needs, user preference, etc., other layers, such as multiple insoles, multiple linings, multiple stiffeners, multiple paddings, multiple sole plates, multiple balancers, multiple layers and/or placements of toe-filler, other layers, fewer layers, etc., may suffice.

FIG. 7A shows an isometric view illustrating partial-foot positive cast 300.

FIG. 7B shows an isometric view illustrating partial-foot positive cast 300 having applied insole 310, inner lining 320, balancer 350, and completed toe-filler 325. Preferably, balancer 350 is heat-molded onto inner lining 320 and is then carved and sanded into its final shape. Preferably, balancer 350 adheres to inner lining 320 during the heat-molding process.

FIG. 8 shows a diagram of the method of forming toe-filler 325 on positive cast 300 with insole 310 and inner lining 320. Preferably, after inner lining 320 (at least embodying herein inner lining means for inner lining such at least one pedorthic) has been formed (preferably sewn) around positive cast 300, dam 800 is formed around the missing portions of the lower limb, attached to inner lining 320, as shown. Preferably, dam 800 is at least one flexible, disposable material, such as, preferably, cardboard and/or a thin plastic sheet, etc. Preferably, after dam 800 has been formed, dam 800 is filled with liquid uncured polymer foam 810 (at least embodying herein at least one resilient unitary filler adapted to fill at least one void exterior to such at least one inner lining, and for molding to the shape of such exterior of such at least one inner lining; and at least embodying herein resilient unitary filler means for filling at least one void exterior to such inner lining means, and for molding to the shape of such exterior of such inner lining means), as shown. Preferably, foam 810 comprises polyurethane foam. Most preferably, foam 810 comprises tough, microcellular, flexible, two-component, polyurethane foam. Preferably, polymer foam 810 is then permitted to cure. Preferably, after foam 810 has cured, dam 800 is removed and cured foam 810 is shaped into toe-filler 325 according to the skill of the pedorthic-maker, preferably by carving and sanding (as by a belt sander). Upon reading the teachings of this specification, those with ordinary skill in the art will now understand that, under appropriate circumstances, considering issues such as advances in technology, etc., other materials, such as poured foam rubber, multiple types of foam, other types of polymers, solid flexible polymers, etc., may suffice.

Figure 9:
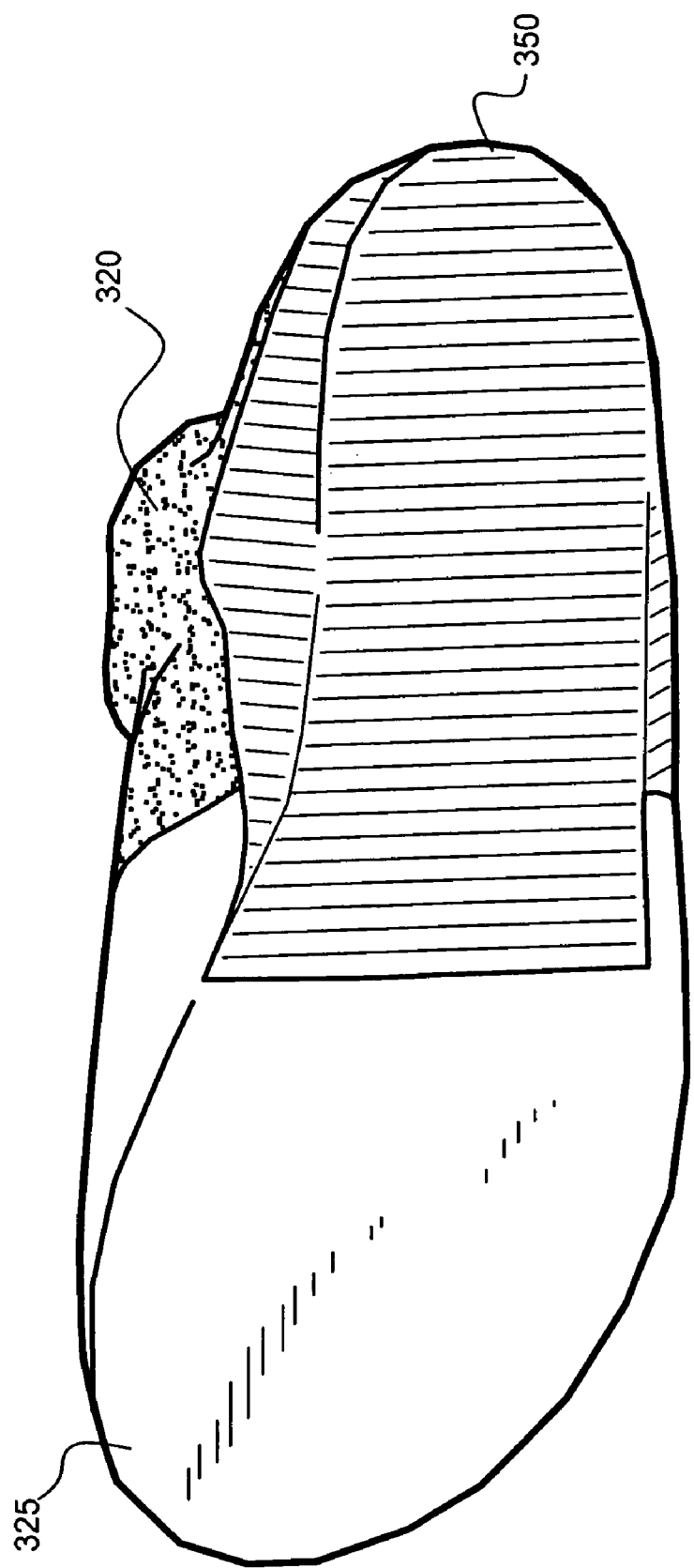
FIG. 9 shows a bottom view illustrating a partial-foot positive cast having an applied insole, inner lining, toe-filler, and balancer.

FIG. 9 shows a bottom view illustrating partial-foot positive cast 300 having an applied insole 310 (hidden in this view), inner lining 320, toe-filler 325, and balancer 350. Preferably, depending on the particular needs of the patient, toe-filler 325 is formed prior to forming balancer 350, as shown. Preferably, balancer 350 is applied to the bottom of inner lining 320 and toe-filler 325 to provide heel and arch support and a flat and balanced walking surface at the heel, as shown.

Figure 10:
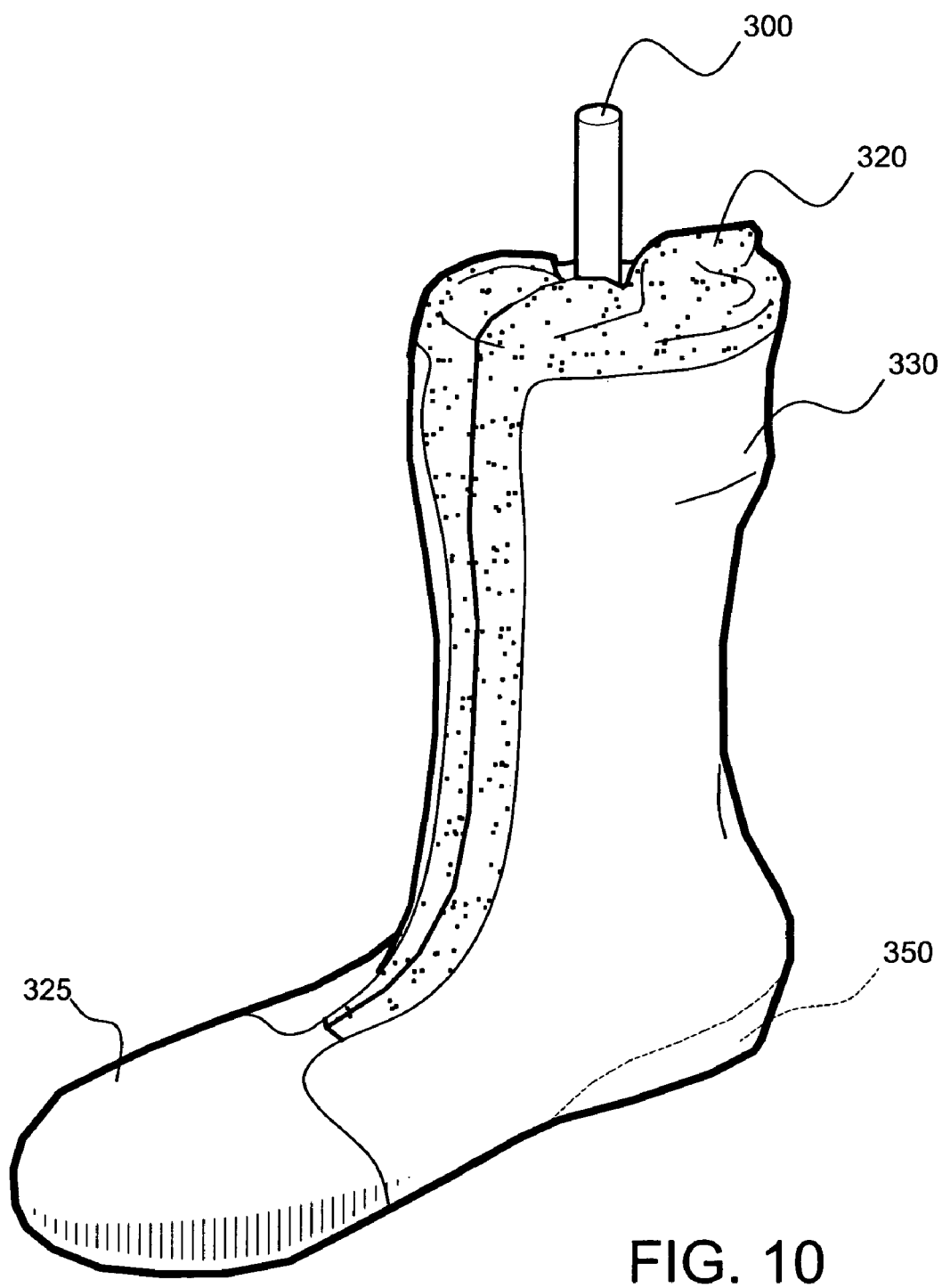
FIG. 10 shows an isometric view illustrating a positive cast of a foot having an applied insole, inner lining, balancer, and padding.

FIG. 10 shows an isometric view illustrating positive cast 300 of a foot having an applied insole 310 (hidden in this view), balancer 350, toe-filler 325, inner lining 320, and padding 330, as shown. Preferably, padding 330 is thermoformed over inner lining 320, toe-filler 325, and balancer 350, as shown.

Figure 11:
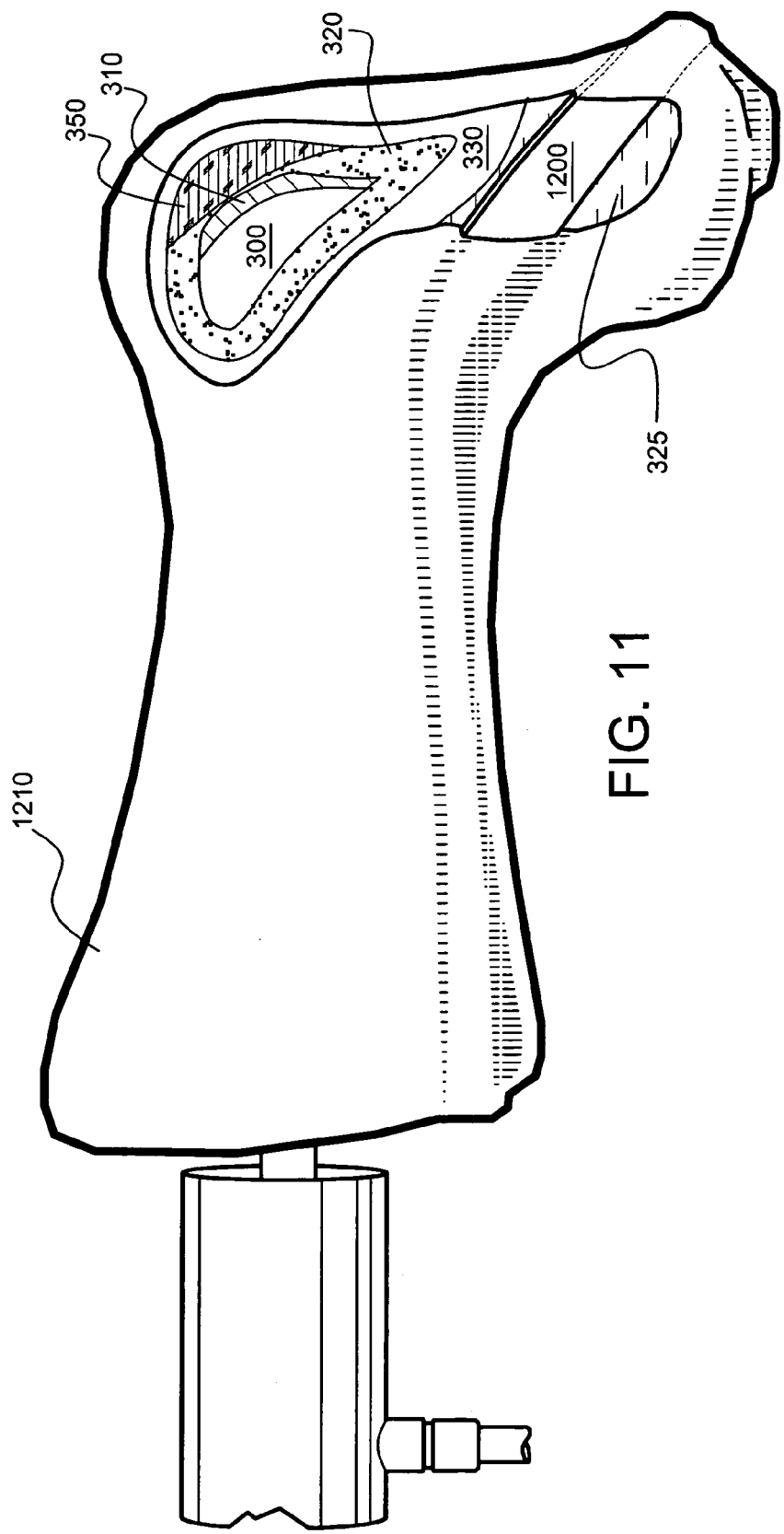
FIG. 11 shows a side view illustrating a positive cast of a partial-foot having an applied insole, inner lining, toe-filler, padding, trim strips, and non-stick stocking.

FIG. 11 shows a side view partially in section illustrating positive cast 300 of a partial-foot having an applied insole 310, inner lining 320, toe-filler 325, balancer 350, padding 330, trim strips 1200, and non-stick stocking 1210. Preferably, after padding 330 is applied to inner lining 320, trim strips 1200 are applied to provide raised areas of the stiffener 340, as shown. These raised areas provide convenient places for stiffener 340 to be cut off of cast 300, preferably with a plaster-cast saw, without cutting the underlying padding 330 and inner lining 320. Preferably, after trim strips 1200 are applied (preferably adhered), non-stick stocking 1210 is applied, as shown, in order to prevent stiffener 340 from sticking to the underlying layers while stiffener 340 is being thermoformed. Preferably, non-stick stocking 1210 comprises a nylon stocking sprinkled liberally with talc and/or cornstarch, as shown. Upon reading the teachings of this specification, those with ordinary skill in the art will now understand that, under appropriate circumstances, considering issues such as advances in technology, etc., other stiffener cutting methods, such as scissors, heated blades, etc., may suffice.

Figure 12:
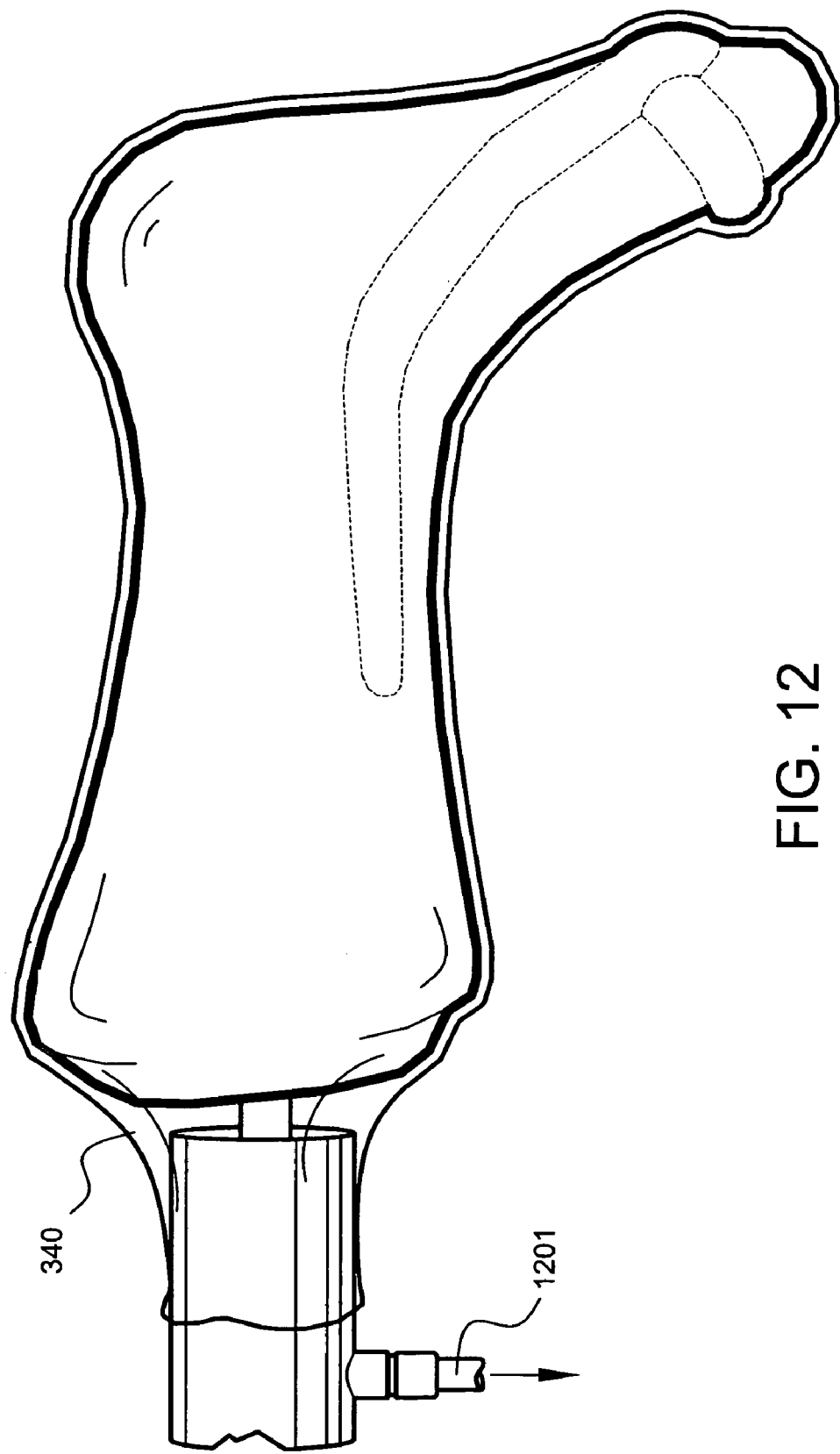
FIG. 12 shows a side view illustrating the process of thermoforming a stiffener onto the positive cast of FIG. 11.

FIG. 12 shows a side view illustrating the process of thermoforming stiffener 340 onto the positive cast 300 of FIG. 11. Preferably, a sheet of thermoplastic is heated to pliability and is draped over positive cast 300 to form stiffener 340, as shown. The sheet of thermoplastic is sealed at the edges and vacuum shaped (using vacuum hose 1201) to the shape of positive cast 300 and the prior-applied layers, as shown.

Figure 13:
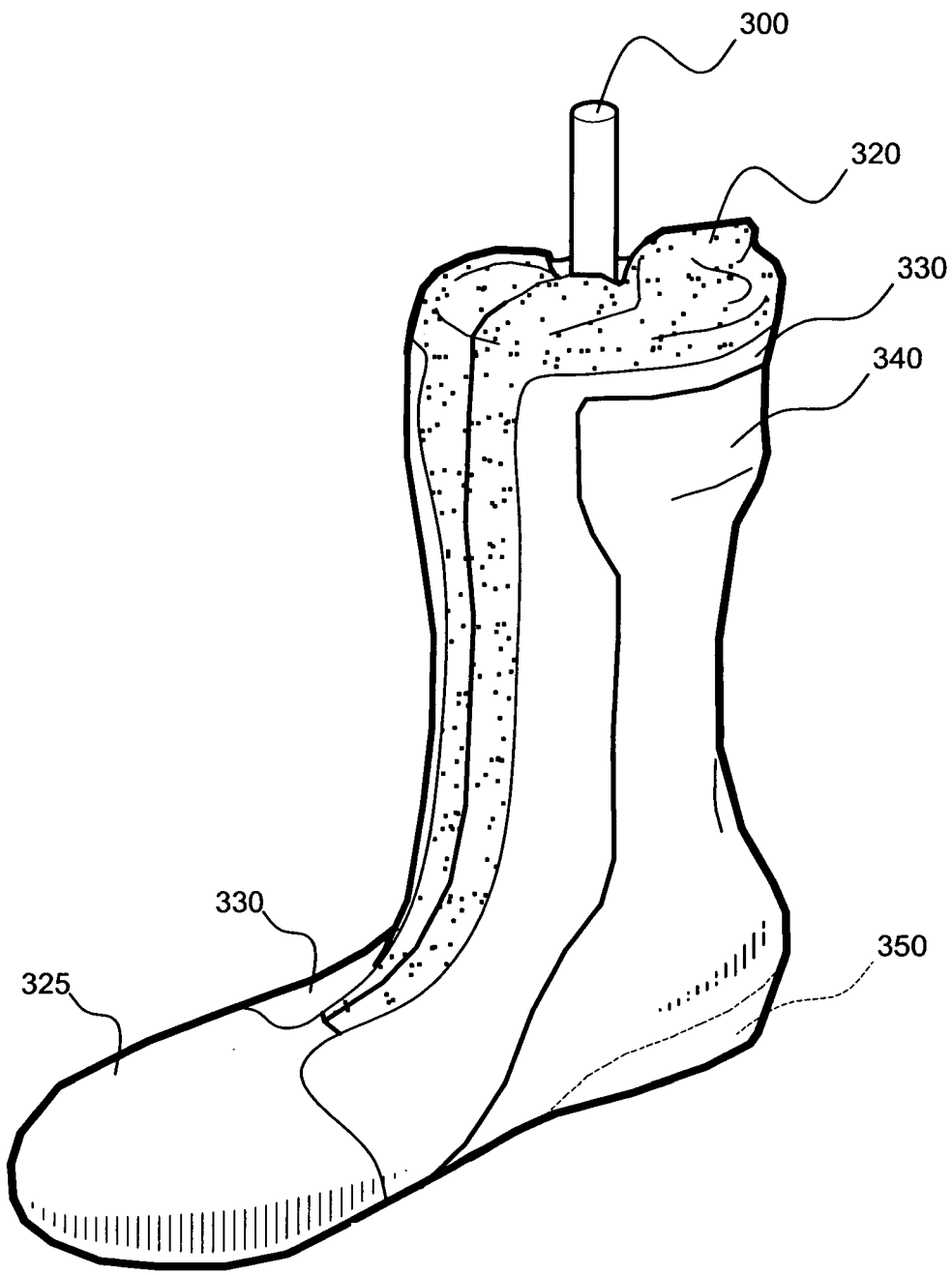
FIG. 13 shows an isometric view illustrating the positive cast with applied inner lining, padding, trimmed stiffener, and toe-filler.

FIG. 13 shows an isometric view illustrating positive cast 300 with applied inner lining 320, padding 330, trimmed stiffener 340, balancer 350, and toe-filler 325. Preferably, after stiffener 340 has cooled, the raised areas over trim strips 1200 are cut, preferably with a plaster-cast saw, and stiffener 340 is temporarily removed from positive cast 300. Stiffener 340 is then trimmed and the edges are smoothed and shaped, according to the desire of the pedorthist. The finished stiffener 340 is then replaced onto positive cast 300, over the underlying layers, as shown. Preferably, stiffener 340 is glued to the underlying layers.

FIG. 14 shows a partially exploded view illustrating positive cast 300 with applied inner lining 320, padding 330, trimmed stiffener 340, sole-plate 360, outer lining 370, and sole 380. Preferably, sole-plate 360 (at least embodying herein wherein such at least one spring comprises at least one carbon fiber plate) comprises at least one strong, springy material, preferably carbon-fiber laminate, as shown. Preferably, for improved pedorthic 110 durability, sole-plate 360 comprises Springlite Carbon Fiber Laminate, manufactured by Otto Bock, of Minneapolis, Minn., as shown. Preferably, if needed, an additional balancing layer 1560 of moldable cork material is used to flatten the bottom of stiffener 340 prior to applying sole-plate 360, as shown in FIG. 3. Upon reading the teachings of this specification, those with ordinary skill in the art will now understand that, under appropriate circumstances, considering issues such as advances in technology, etc., other sole-plate materials, such as other carbon-fiber laminates, metal, plastic, fiberglass, etc., may suffice.

FIG. 15 shows a bottom view illustrating a completed partial-foot Ankle-Foot Orthosis ((AFO) pedorthic 134 with the sole 380 peeled back to reveal sole-plate 360. Preferably, for partial foot AFO pedorthic 134, sole 380 comprises a layer of leather. In a preferred alternate embodiment, an additional layer of thermoplastic cork forming midsole 351 (at least embodying herein at least one midsole adapted to midsole such at least one pedorthic, wherein such at least one midsole substantially underlies such at least one spring on the bottom of such at least one pedorthic, and wherein such at least one sole substantially underlies such at least one midsole; and at least embodying herein midsole means for mid-soling such at least one pedorthic, wherein such midsole means substantially underlies such spring means on the bottom of such at least one pedorthic, and wherein such sole means substantially underlies such midsole means) is applied over spring-plate 360 prior to applying sole 380.

FIG. 16 shows a front view illustrating a nearly-completed neuro-walker pedorthic 122, showing removable insole 310, as shown. Preferably, insole 310 is adhered to inner lining 320. More preferably, insole 310 (at least embodying herein insole means for supporting to at least one lower limb in such at least one pedorthic) is removable and replaceable, as shown.

Figure 17:
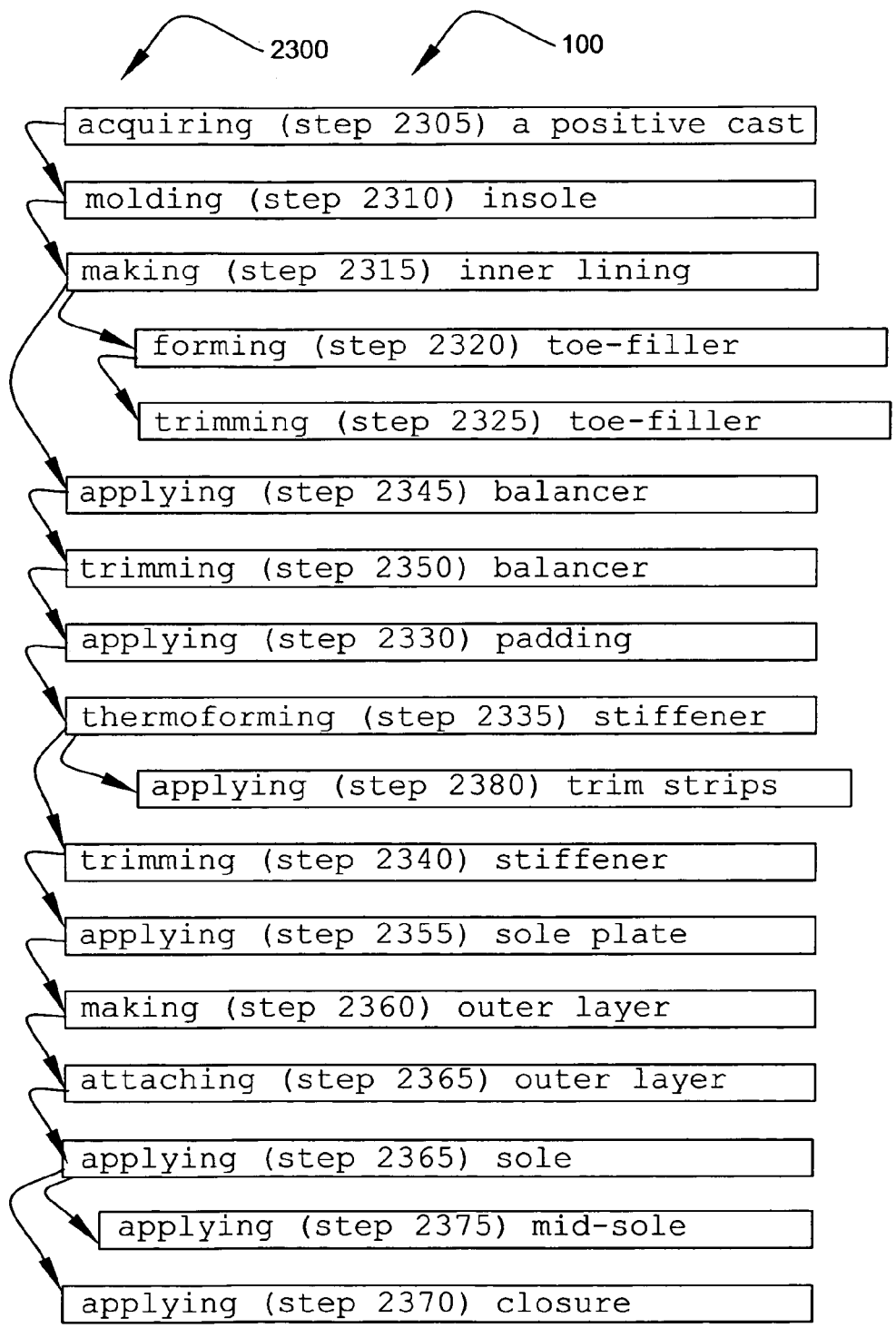
FIG. 17 shows a flow diagram of a method of manufacturing pedorthics according to a preferred embodiment of the present invention.

FIG. 17 shows a flow diagram of method 2300 of manufacturing pedorthics. Preferably, pedorthic system 100 comprises method 2300, as shown. Preferably, method 2300 comprises the steps of: acquiring (step 2305) positive cast 300 of such at least one patient's lower limb; molding (step 2310) insole 310 to the shape of the bottom of positive cast 300 of such at least one patient's lower limb; making (step 2315) and applying inner lining 320 to fit over insole 310 and positive cast 300; applying (step 2345) balancer 350 to at least the bottom of inner lining 320; trimming (step 2350) balancer 350 to provide at least one substantially flat and balanced bottom surface; applying (step 2330) padding 330 at least onto inner lining 320; thermoforming (step 2335) stiffener 340 onto positive cast 300 and the prior-made layers; trimming (step 2340) stiffener 340 to the proper shape, permitting access to the lower limb and substantially surrounding the prior-made layers around the lower limb and substantially underlying the prior-made layers along the bottom of such at least one pedorthic; applying (step 2355) sole plate 360 to substantially the entire bottom of stiffener 340; making (step 2360) outer layer 370 to fit substantially over all of the prior-made layers except sole plate 360; attaching (step 2365) outer layer 370 to the prior-made layers, slightly overlapping the bottom of sole plate 360; applying (step 2365) sole 380 to at least the bottom of sole plate 360; and applying (step 2370) at least one closure to such at least one pedorthic, as shown (at least embodying herein acquiring at least one positive cast of such at least one patient's lower limb; molding at least one insole to the shape of such at least one positive cast on the portion of such at least one positive cast representing the bottom of such at least one patient's lower limb; making at least one inner lining and applying such at least one inner lining over the insole and such at least one positive cast; applying at least one balancer to the bottom of such at least one stiffener; trimming such at least one balancer to provide at least one substantially flat end balanced bottom surface; applying at least one layer of padding at least onto substantially the entire inner lining; thermoforming at least one stiffener onto the positive cast and the prior-made layers; trimming such at least one stiffener to at least one shape permitting access to the foot and substantially surrounding the prior-made layers around the lower limb and substantially underlying the prior-made layers along the bottom of such at least one pedorthic; applying at least one spring plate to substantially the entire bottom of such at least one stiffener; making at least one outer layer to fit substantially over all of the prior-made layers but such at least one spring plate; attaching such at least one outer layer to the prior-made layers, slightly overlapping the bottom of the spring plate; applying at least one sole extending over at least the bottom of such at least one spring plate; and applying at least one closure such at least one pedorthic).

Preferably, method 2300 comprises further comprises the steps of forming (step 2320) toe-filler 325, adhered to inner lining 320; and trimming (step 2325) unitary toe-filler 325 to the final desired shape, as shown.

Preferably, method 2300 comprises further comprises the step of applying (step 2375) at least one mid-sole 351 to at least the bottom of sole plate 360, as shown (at least embodying herein the step of applying at least one midsole to at least the bottom of such at least one spring plate).

Preferably, method 2300 comprises further comprises the step of applying (step 2380) trim strips 1200 to positive cast 300 and the prior-made layers prior to thermoforming stiffener 340 onto positive cast 300 and the prior-made layers, as shown (at least embodying herein the step of applying at least one raised cutting guide to such positive cast and the prior-made layers prior to thermoforming such at least one stiffener onto the positive cast and the prior-made layers). Upon reading the teachings of this specification, those with ordinary skill in the art will now understand that, under appropriate circumstances, considering issues such as advances in technology, patient needs, etc., other steps, such as making other layers, trimming and finishing, etc., may suffice.

Figure 18:
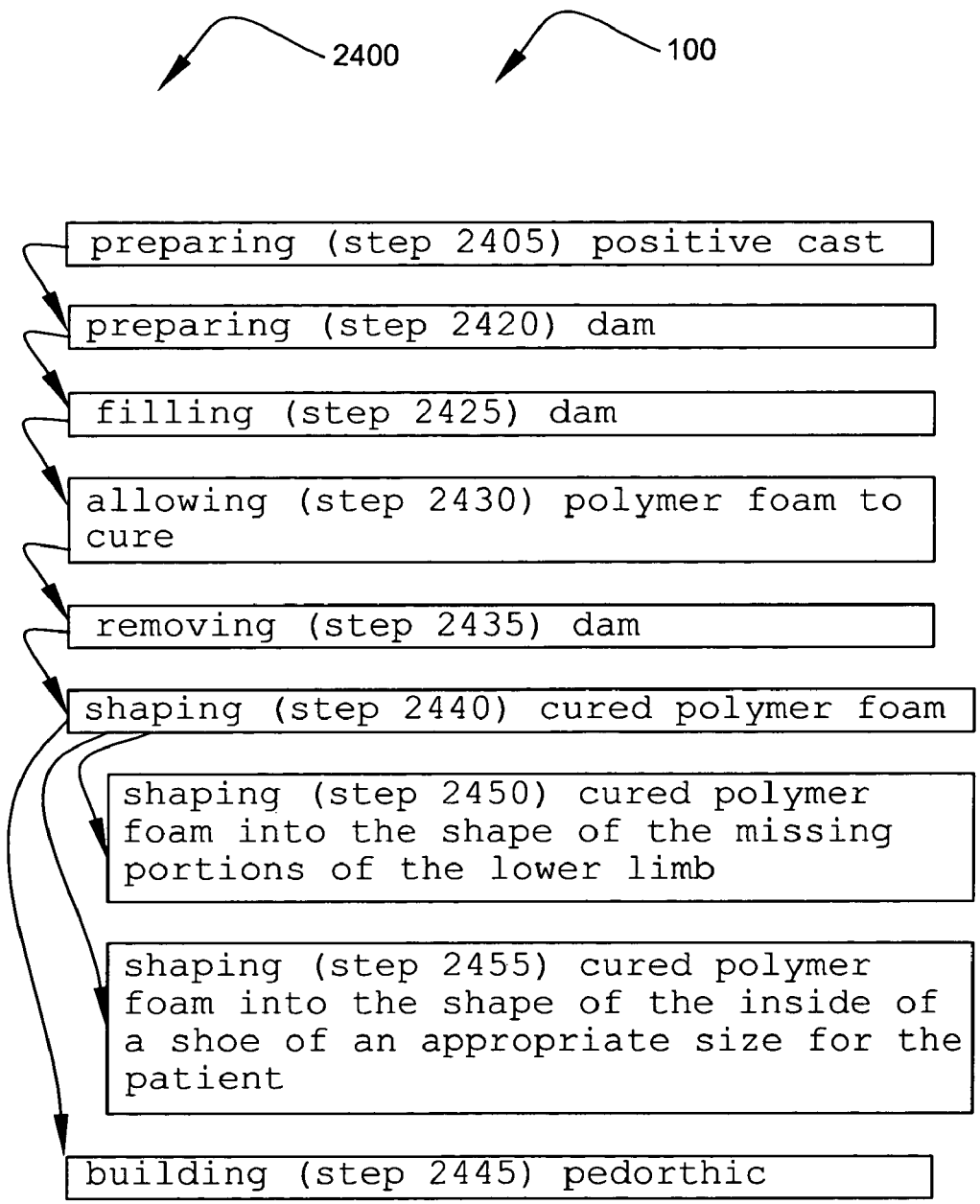
FIG. 18 shows a flow diagram of a method of manufacturing unitary toe-fillers in pedorthics according to a preferred embodiment of the present invention.

FIG. 18 shows a flow diagram of a method of manufacturing unitary toe-fillers 325 in pedorthics 110. Preferably, pedorthic system 100 comprises method 2400, as shown. Preferably, method 2400 comprises the steps of: preparing (step 2405) positive cast 300 of the lower limb; preparing (step 2420) dam 800, attached to inner lining 310, at least surrounding the volume of the missing portions of the lower limb; filling (step 2425) dam 800 with uncured polymer foam 810; allowing (step 2430) polymer foam 810 to cure; removing (step 2435) dam 800; shaping (step 2440) cured polymer foam 810 to the desired shape; and building (step 2445) pedorthic 110 onto shaped polymer foam 810 and inner lining 820, as shown (at least embodying herein preparing at least one positive cast of such at least one lower limb; preparing at least one inner lining surrounding such at least one positive cast of such at least one lower limb; preparing at least one dam, attached to such at least one inner lining, at least surrounding the volume of the missing portions of such at least one lower limb; filling such at least one dam with at least one uncured polyurethane foam; allowing such at least one polyurethane foam to cure; removing such at least one dam; shaping such at least one cured polyurethane foam to the desired shape; building at least one pedorthic onto such at least one shaped polyurethane foam and such at least one inner lining).

Preferably, method 2400 further comprises the step of shaping (step 2450) cured polymer foam 810 into the shape of the missing portions of the lower limb, as shown (at least embodying herein the step of shaping such at least one cured polyurethane foam into the shape of the missing portions of the lower limb).

Preferably, method 2400 further comprises the step of shaping (step 2455) cured polymer foam 810 into the shape of the inside of such at least one shoe of an appropriate size for the patient, as shown (at least embodying herein the step of shaping such at least one cured polyurethane foam into the shape of the inside of such at least one pedorthic of an appropriate size for the patient). Upon reading the teachings of this specification, those with ordinary skill in the art will now understand that, under appropriate circumstances, considering issues such as advances in technology, patient needs, etc., other steps may suffice, such as embedding objects in the foam, using multiple layers of foam, using multiple types of foam, etc., may suffice.

Although applicant has described applicant's preferred embodiments of this invention, it will be understood that the broadest scope of this invention includes such modifications as diverse shapes and sizes and materials. Such scope is limited only by the below claims as read in connection with the above specification. Further, many other advantages of applicant's invention will be apparent to those skilled in the art from the above descriptions and the below claims.

What is claimed is:

1. A pedorthic support system, relating to at least one pedorthic adapted to assist at least one patient requiring lower limb immobilization in order to walk, comprising:
   a) at least one insole adapted to support at least one lower limb in such at least one pedorthic;
   b) at least one inner lining;
   c) wherein said at least one insole is positioned inward of said at least one inner lining;
   d) at least one balancer adapted to balance such at least one pedorthic, wherein said at least one balancer underlies heel and arch portions of said at least one inner lining on the bottom of such at least one pedorthic;
   e) at least one padding adapted to pad such at least one pedorthic;
   f) wherein said at least one balancer, said at least one inner lining, and said at least one insole are positioned inward of said at least one padding;
   g) at least one stiffener adapted to stiffly support the lower limb and the foot in such at least one pedorthic
      i) wherein said at least one padding, said at least one balancer, said at least one inner lining, and said at least one insole are positioned inward of said at least one stiffener, and
      ii) wherein said at least one stiffener extends forward to the toe-end of such at least one pedorthic along the bottom of such at least one pedorthic;
   h) at least one spring adapted to spring such at least one pedorthic, wherein said at least one spring underlies said at least one stiffener;
   i) at least one outer lining, wherein said at least one outer lining covers the exterior surface of such at least one pedorthic; and
   j) at least one closure adapted to close such at least one pedorthic.

2. The pedorthic support system, according to claim 1, further comprising at least one resilient unitary filler adapted to fill at least one void exterior to said at least one inner lining, and adapted to mold to the shape of such exterior of said at least one inner lining.

3. The pedorthic support system, according to claim 1, further comprising at least one sole, wherein said at least one sole substantially underlies said at least one spring on the bottom of such at least one pedorthic.

4. The pedorthic support system, according to claim 3, further comprising at least one midsole, wherein said at least one midsole substantially underlies said at least one spring on the bottom of such at least one pedorthic, and wherein said at least one sole substantially underlies said at least one midsole.

5. A pedorthic support system, relating to at least one pedorthic adapted to assist at least one patient requiring lower limb immobilization in order to walk, comprising:
   a) at least one insole adapted to support at least one lower limb in such at least one pedorthic, wherein said at least one insole is custom-molded to the shape of the bottom of such at least one patient's lower limb;
   b) at least one inner lining
      ii) wherein said at least one inner lining is custom shaped to fit around at least said at least one insole and at least one portion of such at least one patient's lower limb;
   c) wherein said at least one insole is positioned inward of said at least one inner lining;
   d) at least one padding adapted to pad such at least one pedorthic;
   e) wherein said at least one inner lining and said at least one insole are positioned inward of said at least one padding;
   f) at least one stiffener adapted to stiffly support the lower limb in such at least one pedorthic
      i) wherein said at least one padding is positioned inward of said at least one stiffener,
      ii) wherein said at least one stiffener is custom-molded to the shape of the at least one underlying layer(s), and
      iii) wherein said at least one stiffener extends forward to the toe-end of such at least one pedorthic along the bottom of such at least one pedorthic;
   g) at least one balancer adapted to balance such at least one pedorthic, wherein said at least one balancer underlies heel and arch portions of said at least one stiffener on the bottom of said at least one inner lining;
   h) at least one spring adapted to spring such at least one pedorthic, wherein said at least one spring underlies said at least one stiffener;
   i) at least one outer lining, wherein said at least one outer lining covers the exterior surface of such at least one pedorthic; and
   j) at least one closure adapted to close such at least one pedorthic.

6. The pedorthic support system, according to claim 5, further comprising at least one resilient unitary filler adapted to fill at least one void exterior to said at least one inner lining, and adapted to mold to the shape of such exterior of said at least one inner lining.

7. The pedorthic support system, according to claim 6, wherein said at least one resilient unitary filler comprises at least one polyurethane foam.

8. The pedorthic support system, according to claim 6, wherein said at least one resilient unitary filler comprises at least one tough, microcellular, flexible, two-component, polyurethane foam.

9. The pedorthic support system, according to claim 5, further comprising at least one sole, wherein said at least one sole substantially underlies said at least one spring on the bottom of such at least one pedorthic.

10. The pedorthic support system, according to claim 9, wherein said at least one sole comprises at least one leather.

11. The pedorthic support system, according to claim 9, wherein said at least one sole comprises at least one plastic.

12. The pedorthic support system, according to claim 9, further comprising at least one midsole, wherein said at least one midsole substantially underlies said at least one spring on the bottom of such at least one pedorthic, and wherein said at least one sole substantially underlies said at least one midsole.

13. The pedorthic support system, according to claim 5, wherein said at least one insole comprises at least one thermoplastic foam.

14. The pedorthic support system, according to claim 5, wherein said at least one inner lining comprises at least one leather.

15. The pedorthic support system, according to claim 5, wherein said at least one padding comprises at least one thermoplastic foam.

16. The pedorthic support system, according to claim 5, wherein said at least one stiffener substantially comprises at least one thermoformable polyethylene sheet material.

17. The pedorthic support system, according to claim 5, wherein said at least one balancer comprises cork in at least one thermoplastic matrix.

18. The pedorthic support system, according to claim 5, wherein said at least one spring comprises at least one carbon fiber plate.

19. The pedorthic support system, according to claim 18, wherein said at least one carbon fiber plate comprises at least one carbon-fiber laminate.

20. The pedorthic support system, according to claim 5, wherein said at least one outer lining comprises at least one leather.

21. A pedorthic support system, relating to at least one pedorthic adapted to assist at least one patient requiring lower limb immobilization in order to walk, comprising:
   a) at least one insole adapted to support at least one lower limb in such at least one pedorthic, wherein said at least one insole is custom-molded to the shape of the bottom of such at least one patient's lower limb;
   b) at least one inner lining
      ii) wherein said at least one inner lining is custom shaped to fit around at least said at least one insole and at least one portion of such at least one patient's lower limb;
   c) wherein said at least one insole is positioned inward of said at least one inner lining;
   d) at least one balancer adapted to balance such at least one pedorthic, wherein said at least one balancer underlies heel and arch portions of said at least one inner lining on the bottom of such at least one pedorthic;
   e) at least one padding adapted to pad such at least one pedorthic;
   f) wherein said at least one balancer, said at least one inner lining, and said at least one insole are positioned inward of said at least one padding;
   g) at least one stiffener adapted to stiffly support the lower limb in such at least one pedorthic
      i) wherein said at least one padding, said at least one balancer, said at least one inner lining, and said at least one insole are positioned inward of said at least one stiffener substantially surrounds said at least one padding,
      ii) wherein said at least one stiffener is custom-molded to the shape of the underlying layer(s), and
      iii) wherein said at least one stiffener extends forward substantially to the toe-end of such at least one pedorthic along the bottom of such at least one pedorthic;
   h) at least one spring, wherein said at least one spring underlies said at least one stiffener;
   i) at least one outer lining, wherein said at least one outer lining covers the exterior surface of such at least one pedorthic;

j) at least one sole, wherein said at least one sole underlies said at least one spring on the bottom of such at least one pedorthic; and k) at least one closure adapted to close such at least one pedorthic.

22. A pedorthic support system, relating to at least one pedorthic adapted to assist at least one patient requiring lower limb immobilization in order to walk, comprising:

a) at least one insole adapted to support at least one lower limb in such at least one pedorthic, wherein said at least one insole is custom-molded to the shape of the bottom of such at least one patient's lower limb;

b) at least one inner lining ii) wherein said at least one inner lining is custom shaped to fit around at least said at least one insole and at least one portion of such at least one patient's lower limb;

c) wherein said at least one insole is positioned inward of said at least one inner lining;

d) at least one balancer adapted to balance such at least one pedorthic, wherein said at least one balancer underlies heel and arch portions of said at least one inner lining on the bottom of such at least one pedorthic;

e) at least one padding adapted to pad such at least one pedorthic;

f) wherein said at least one balancer, said at least one inner lining, and said at least one insole are positioned inward of said at least one padding;

g) at least one stiffener adapted to stiffly support the lower limb in such at least one pedorthic i) wherein said at least one padding, said at least one balancer, said at least one inner lining, and said at least one insole are positioned inward of said at least one stiffener, ii) wherein said at least one stiffener is custom-molded to the shape of the underlying layers, iii) wherein said at least one stiffener extends forward to the toe-end of such at least one pedorthic along the bottom of such at least one pedorthic, and iv) wherein said at least one stiffener extends upward at least to the top edge of said at least one insole at the toe-end of such at least one pedorthic;

h) at least one spring adapted to spring such at least one pedorthic, wherein said at least one spring underlies said at least one stiffener;

i) at least one outer lining, wherein said at least one outer lining covers the exterior surface of such at least one pedorthic;

j) at least one sole, wherein said at least one sole underlies said at least one spring on the bottom of such at least one pedorthic; and k) at least one closure adapted to close such at least one pedorthic;

l) wherein such at least one pedorthic is substantially open over such at least one patient's toes.

23. A pedorthic support system, relating to at least one pedorthic adapted to assist at least one patient requiring lower limb immobilization in order to walk, comprising:

a) at least one insole adapted to support at least one lower limb in such at least one pedorthic, wherein said at least one insole is custom-molded to the shape of the bottom of such at least one patient's lower limb;

i) at least one inner lining, and ii) wherein said at least one insole is positioned inward of said at least one inner lining;

iii) wherein said at least one inner lining is custom shaped to fit around at least said at least one insole and at least one portion of such at least one patient's lower limb;

b) at least one resilient unitary filler adapted to fill at least one void exterior to said at least one inner lining, and adapted to mold to the shape of such exterior of said at least one inner lining;

c) at least one balancer adapted to balance such at least one pedorthic, wherein said at least one balancer underlies heel and arch portions of said at least one inner lining on the bottom of such at least one pedorthic;

d) at least one padding adapted to pad such at least one pedorthic;

e) wherein said at least one balancer, said at least one inner lining, and said at least one insole are positioned inward of said at least one padding;

f) at least one stiffener adapted to stiffly support the lower limb in such at least one pedorthic i) wherein said at least one padding, said at least one balancer, said at least one inner lining, and said at least one insole are positioned inward of said at least one stiffener, ii) wherein said at least one stiffener is custom-molded to the shape of the underlying layers, and iii) wherein said at least one stiffener extends forward to the toe-end of such at least one pedorthic along the bottom of such at least one pedorthic;

g) at least one spring adapted to spring such at least one pedorthic, wherein said at least one spring underlies said at least one stiffener;

h) at least one outer lining, wherein said at least one outer lining covers the exterior surface of such at least one pedorthic;

i) at least one sole, wherein said at least one sole underlies said at least one spring on the bottom of such at least one pedorthic; and j) at least one closure adapted to close such at least one pedorthic.

24. The pedorthic support system, according to claim 23, wherein such at least one pedorthic is sized and shaped to fit into at least one non-custom shoe purchased by the patient.

* * * * *